(12) United States Patent
Hara et al.

(10) Patent No.: US 9,607,208 B2
(45) Date of Patent: Mar. 28, 2017

(54) ANALYZING A SKIN CONDITION FROM A VIDEO

(71) Applicant: SHISEIDO COMPANY, LTD., Tokyo (JP)

(72) Inventors: Yusuke Hara, Kanagawa (JP); Ichiro Iwai, Kanagawa (JP); Hiroyuki Ohnishi, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/779,722

(22) PCT Filed: Feb. 27, 2014

(86) PCT No.: PCT/JP2014/054938
§ 371 (c)(1),
(2) Date: Sep. 24, 2015

(87) PCT Pub. No.: WO2014/156461
PCT Pub. Date: Oct. 2, 2014

(65) Prior Publication Data
US 2016/0063312 A1    Mar. 3, 2016

(30) Foreign Application Priority Data
Mar. 28, 2013 (JP) ................................ 2013-070061

(51) Int. Cl.
*G06K 9/00* (2006.01)
*A61B 5/00* (2006.01)
(Continued)

(52) U.S. Cl.
CPC ........ *G06K 9/00268* (2013.01); *A61B 5/0077* (2013.01); *A61B 5/1079* (2013.01);
(Continued)

(58) Field of Classification Search
None
See application file for complete search history.

(56) References Cited

U.S. PATENT DOCUMENTS

2007/0125390 A1    6/2007  Afriat et al.
2008/0176077 A1*   7/2008  Doughty .............. A61B 5/0048
                                                     428/409
2009/0195545 A1*   8/2009  Debevec ................ G06T 13/40
                                                     345/473

FOREIGN PATENT DOCUMENTS

JP    H10-043141    2/1998
JP    H11108630     4/1999
(Continued)

OTHER PUBLICATIONS

Task Force Committee for Evaluation of Anti-aging function, "Guideline for Evaluation of Anti-wrinkle Products", Journal of Japanese Cosmetic Science Society, vol. 30, No. 4, pp. 316-332 (2006) (with partial English translation).
Hara, Y., "Development of New Evaluation Method Based on Characterization of Each Crow's Feet Wrinkle by Three-Dimensional Analysis", Journal of Japanese Cosmetic Science Society, vol. 35, No. 2, pp. 93-98 (2011).
(Continued)

*Primary Examiner* — Atiba O Fitzpatrick
(74) *Attorney, Agent, or Firm* — IPUSA, PLLC

(57) ABSTRACT

An image analysis apparatus that analyzes a skin condition from a video of the face of a subject captured with an imaging part includes a tracking part configured to track the amount of changes of multiple tracking points arranged in advance in an analysis region of the face based on a change in the expression of the face included in the video, and obtain the compression ratio of the skin in the analysis region based on the amount of changes, and a skin condition analysis part configured to analyze the skin condition of the subject based on the compression ratio obtained by the tracking part.

9 Claims, 18 Drawing Sheets

(51) Int. Cl.
  *A61B 5/11* (2006.01)
  *A61B 19/00* (2006.01)
  *G06K 9/46* (2006.01)
  *G06T 7/20* (2017.01)
  *A61B 5/107* (2006.01)
  *G06T 7/246* (2017.01)

(52) U.S. Cl.
  CPC ............ *A61B 5/1128* (2013.01); *A61B 5/442* (2013.01); *A61B 19/5212* (2013.01); *G06K 9/00315* (2013.01); *G06K 9/46* (2013.01); *G06T 7/20* (2013.01); *G06T 7/248* (2017.01); *A61B 5/7271* (2013.01); *G06K 2009/4666* (2013.01); *G06T 2207/30088* (2013.01)

(56) References Cited

FOREIGN PATENT DOCUMENTS

| JP | 2004-187879 | 7/2004 |
| JP | 2009-153609 | 7/2009 |
| JP | 2011-056189 | 3/2011 |
| JP | 2011-101663 | 5/2011 |

OTHER PUBLICATIONS

International Search Report mailed on May 13, 2014.
Japanese Official Notification dated Oct. 25, 2016.
Motoko Murakami et al., "Analysis of wrinkle formation related to facial skin motion shown by skin surface strain distribution" preliminary release for IFSCC 2012 27th Congress in South Africa, Oct. 18, 2012.
Motoko Murakami et al., "Analysis of wrinkle formation related to facial skin motion shown by skin surface strain distribution" IFSCC 2012 27th Congress in South Africa, Oct. 18, 2012.
Tsutomu Fujiwara (2012). "Investigation of the relationship between wrinkle formation and deformation of the skin using three-dimensional motion analysis." Skin Research and Technology 2013; 19: e318-e324.
Osamu Kuwazuru et al. (2012). "Skin wrinkling morphology changes suddenly in the early 30s." Skin Research and Technology 2012: 18: 495-503.
Extended European Search Report mailed Nov. 2, 2016.
Sung Eun Choi et al: "Age estimation using a hierarchical classifier based on global and local facial features", Pattern Recognition, Elsevier, GB, vol. 44, No. 6, Dec. 7, 2010, pp. 1262-1281, XP028136016.

* cited by examiner

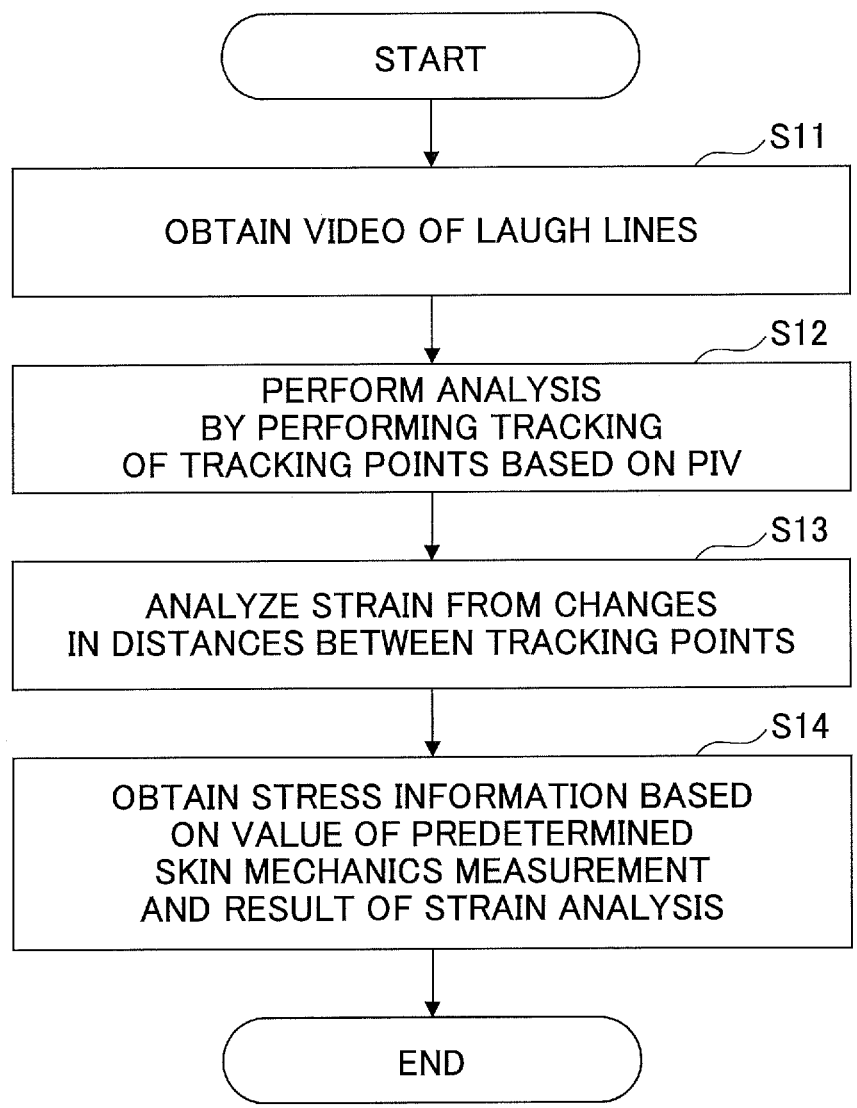

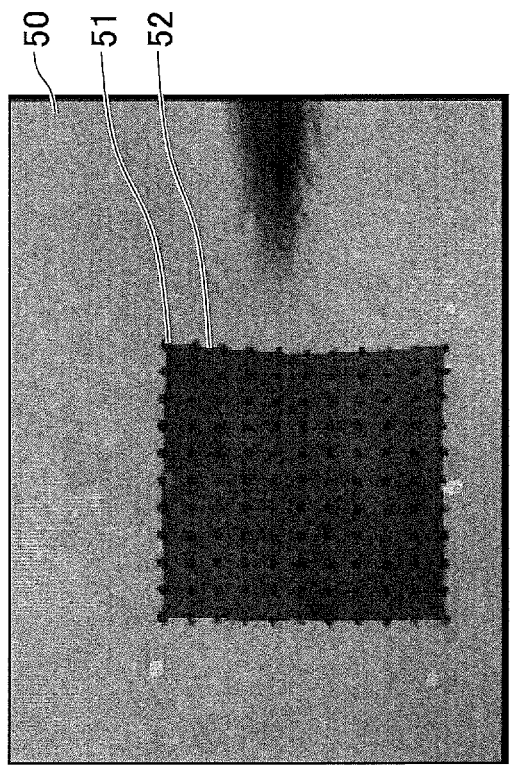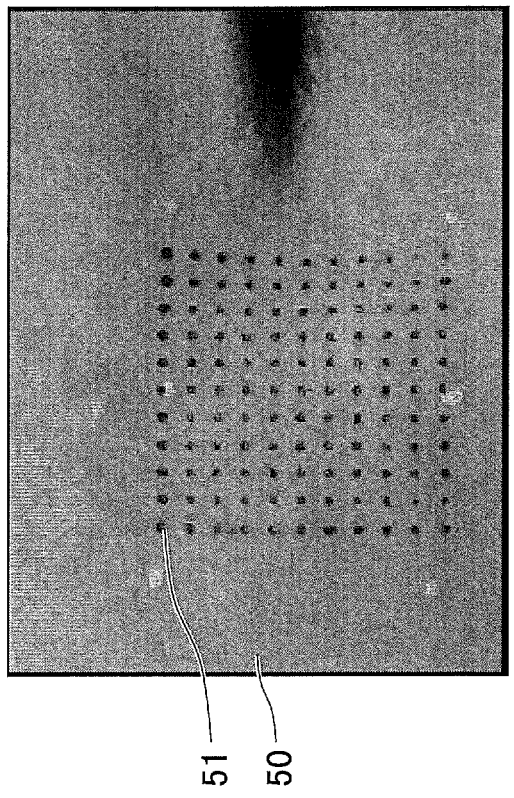

LOCAL COORDINATE SYSTEM

GENERALIZED COORDINATE SYSTEM

● SAMPLING POINT

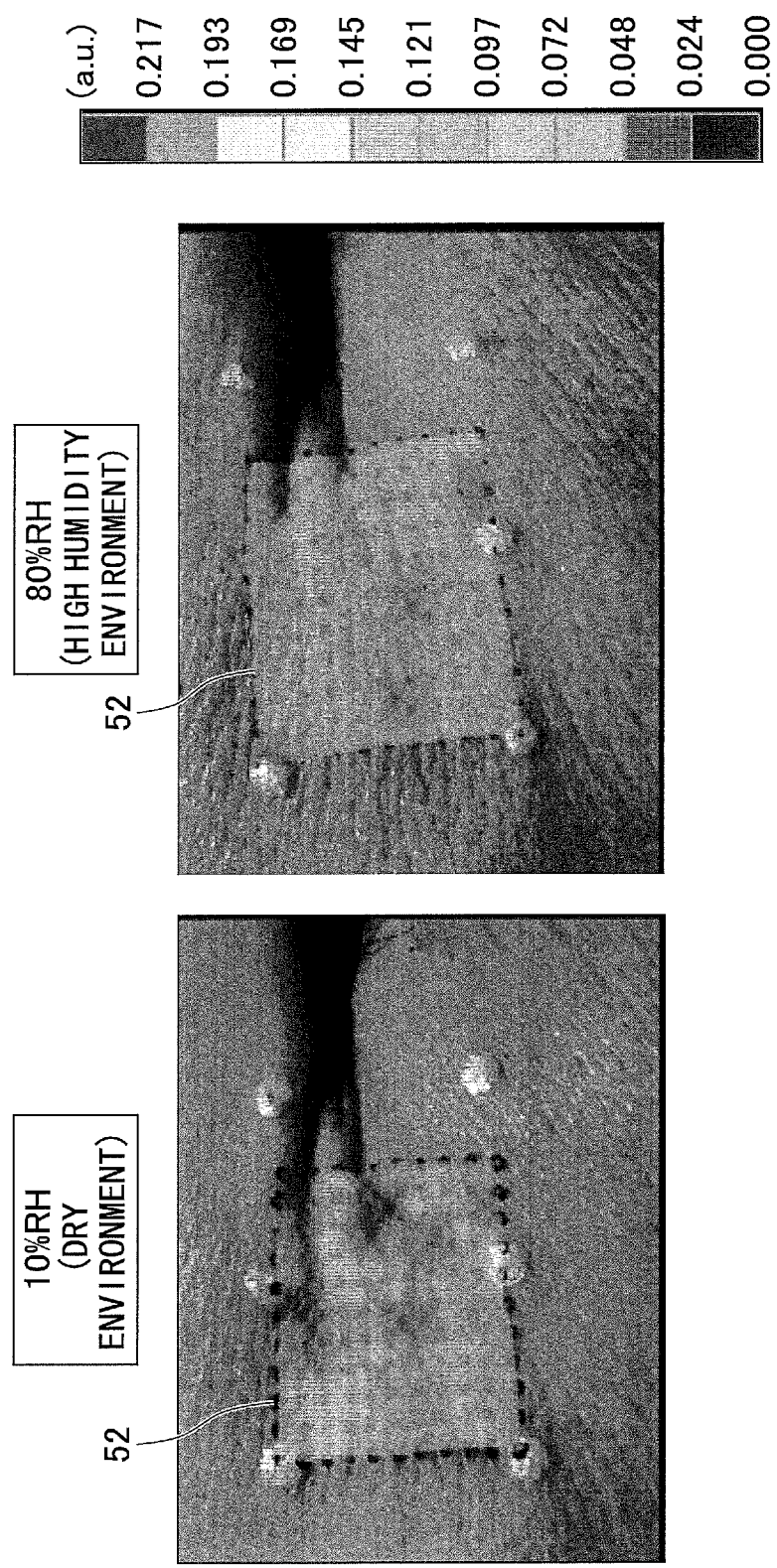

FIG.12A
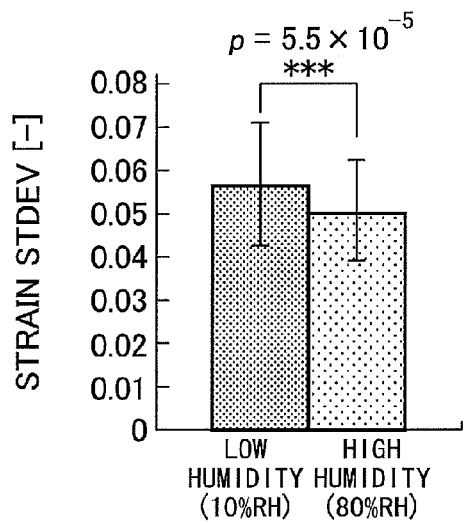
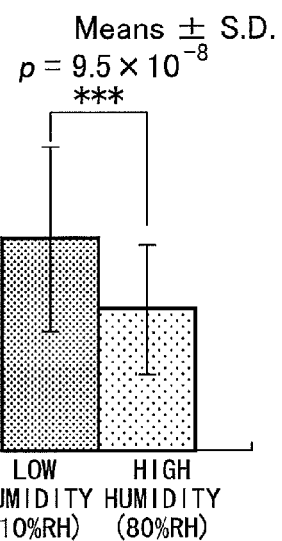
FIG.12B
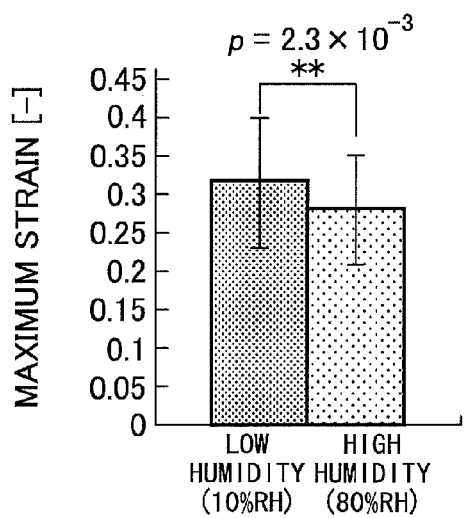
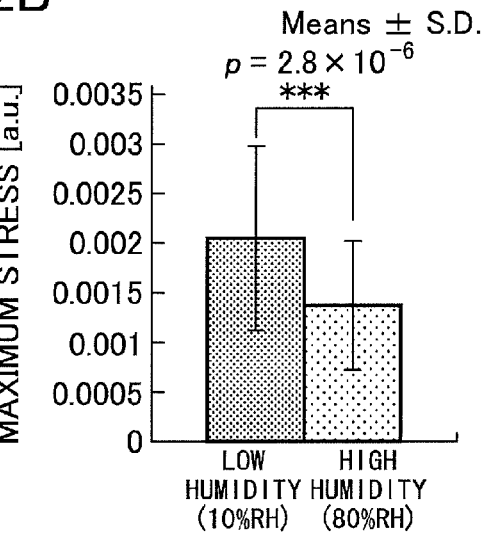
FIG.12C
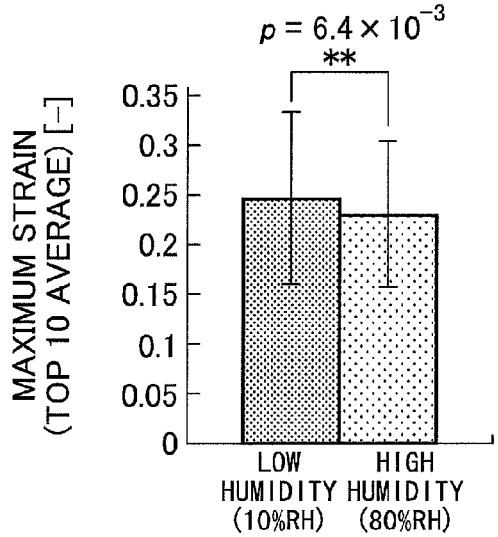
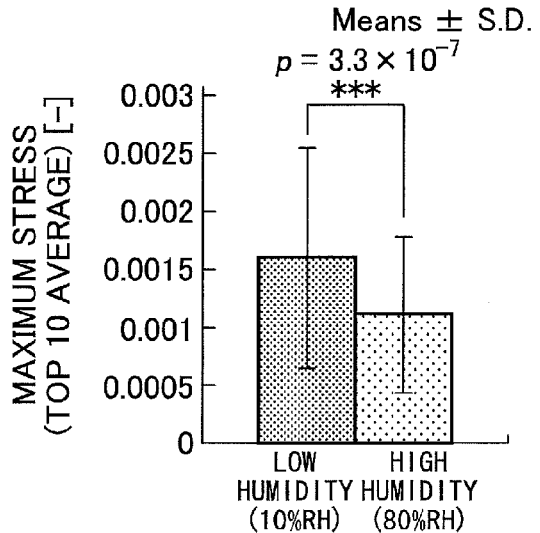

FIG.15
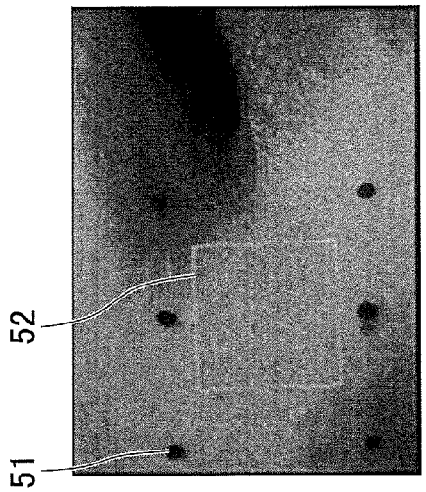
INCONSPICUOUS
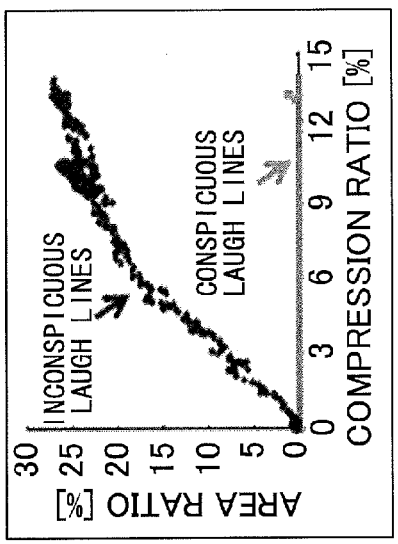
100.0%
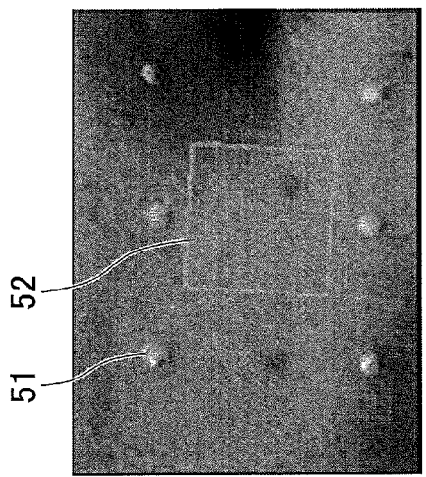
CONSPICUOUS
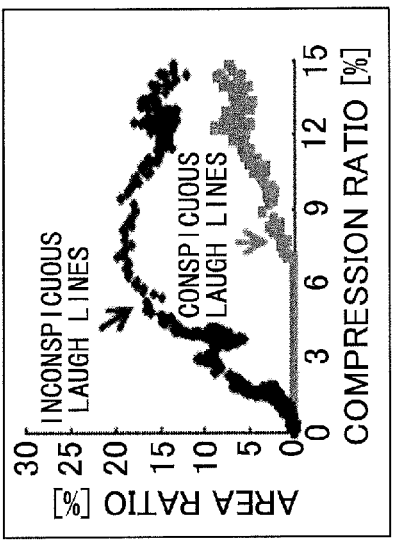
65.0%
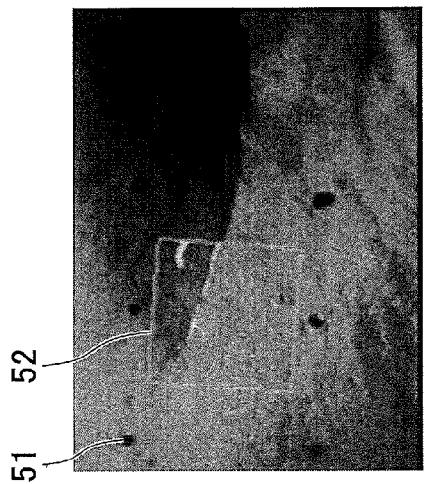
REMARKABLY CONSPICUOUS
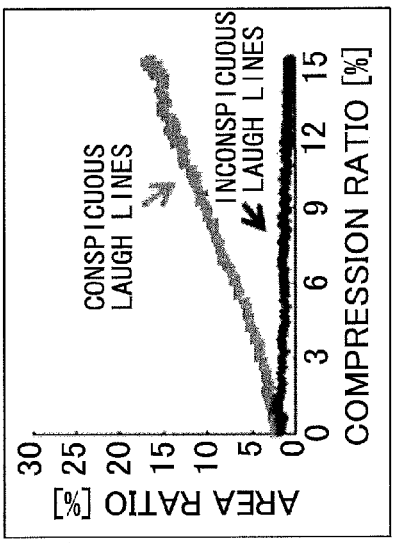
INCONSPICUOUS LAUGH LINES RATIO
4.4%

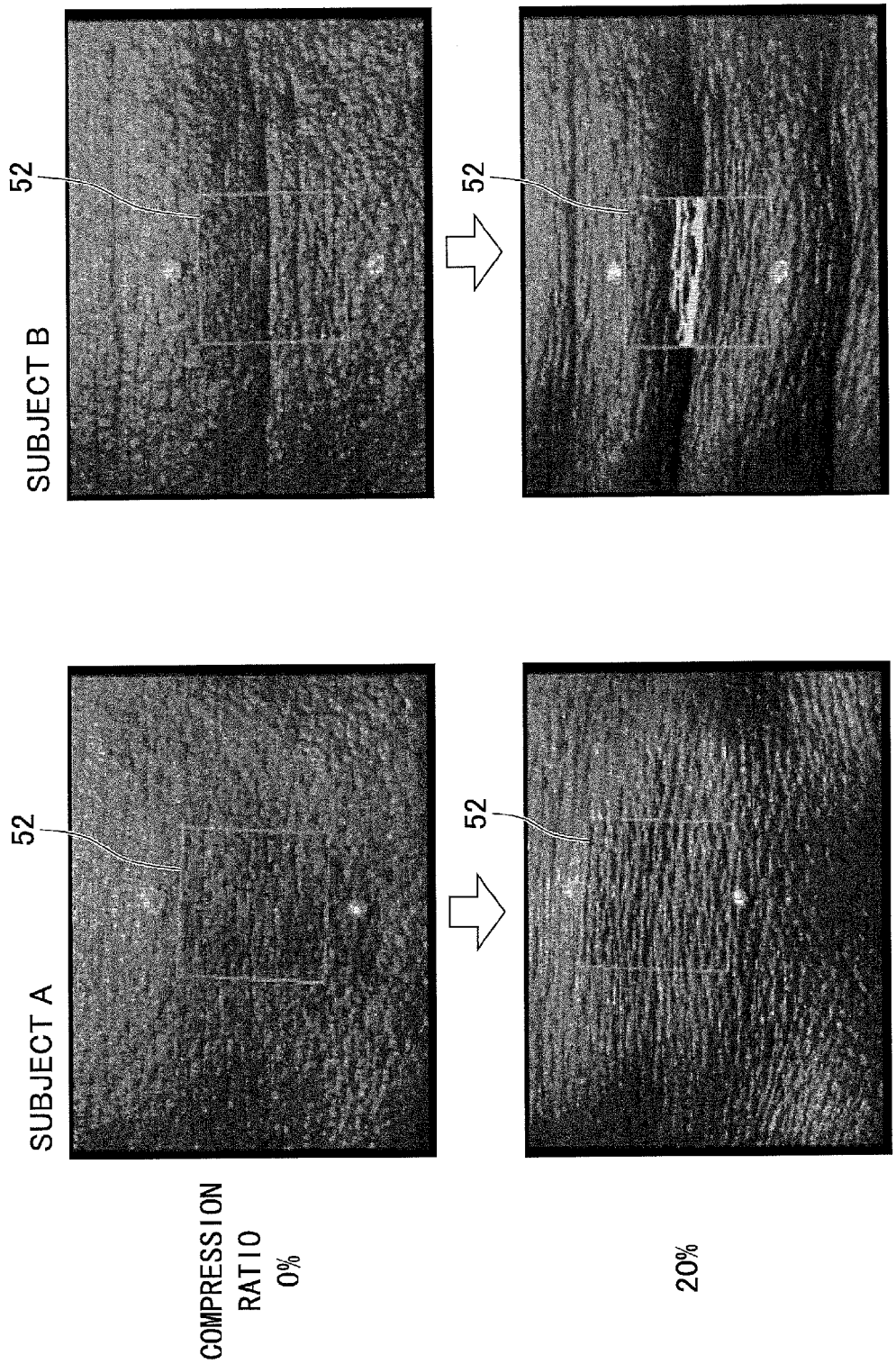

| BARE SKIN | AFTER SKIN CARE |
|---|---|
| 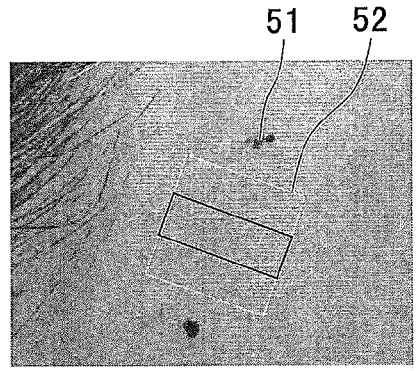 51 52 | 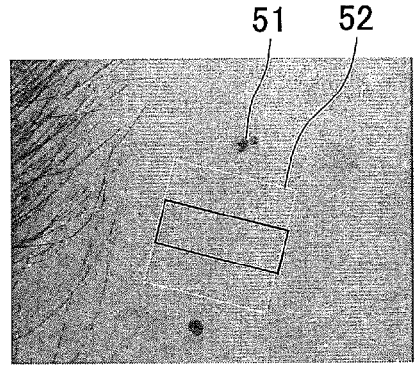 51 52 |
FIG.19B
| BARE SKIN | AFTER SKIN CARE |
|---|---|
| 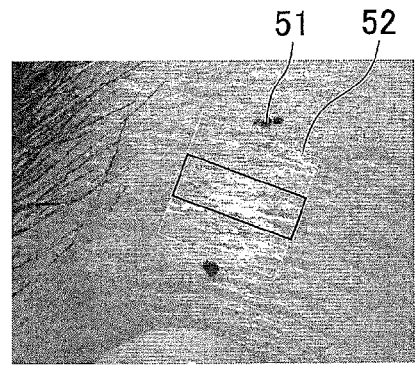 51 52 | 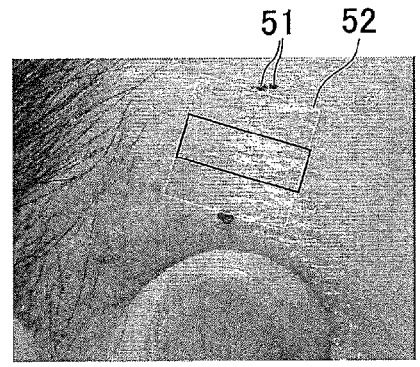 51 52 |
FIG.19C
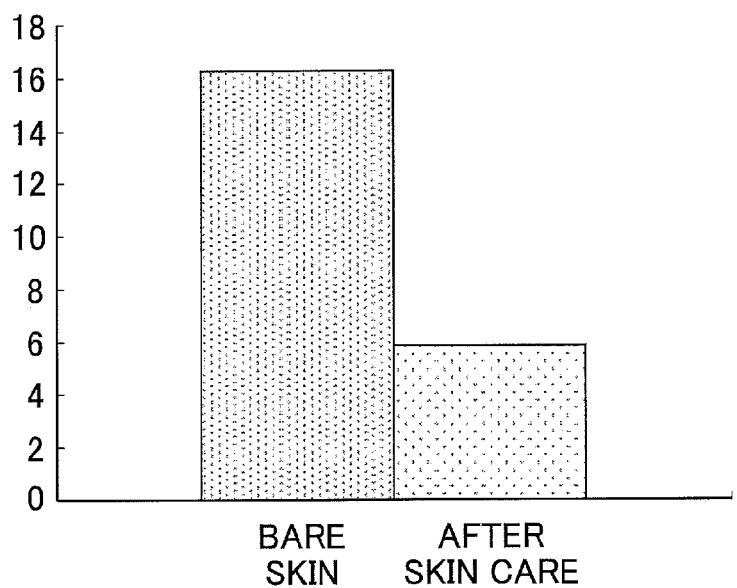

ANALYZING A SKIN CONDITION FROM A VIDEO

TECHNICAL FIELD

An embodiment of the present invention relates to image analysis apparatuses, image analysis methods, and image analysis programs, and in particular, relates to an image analysis apparatus, an image analysis method, and an image analysis program for properly analyzing a skin condition from expression wrinkles of a subject.

BACKGROUND ART

It has been the case that wrinkles formed on the face (such as the outer corners of the eyes and the cheeks) of a subject are caused with a twist due to a change in the facial expression (for example, laugh lines or anger lines) or pressing on the skin. Furthermore, for reasons such as aging or the decline of skin texture or elasticity, wrinkles no longer disappear even when the expression returns (so-called residual wrinkles), so as to ultimately become wrinkles that are caused irrespective of expressions (so-called fixed wrinkles). Accordingly, wrinkles have become a major cosmetic issue as a symbol of the aging phenomena of appearance, so that consumers have expected much from the development of products that are effective in preventing or reducing wrinkles. Furthermore, in the development of anti-wrinkle products, it is important to demonstrate their performance and effects by a scientific and highly-reliable evaluation method.

Therefore, the standardization of a wide variety of wrinkle assessment methods has been performed by creating guidelines for evaluating the functions of anti-wrinkle products for wrinkles at the outer corners of eyes (for example, see Non-Patent Document 1.) Furthermore, there has been the technique of calculating the depth and area of each wrinkle from the three-dimensional shape data of the outer corner of an eye and assessing wrinkles based on a distribution analysis to which the results of a visual assessment are added (for example, see Non-Patent Document 2).

PRIOR ART DOCUMENTS

Non-Patent Documents

[Non-Patent Document 1] Task Force Committee for Evaluation of Anti-aging function, "Guideline for Evaluation of Anti-wrinkle Products," Journal of Japanese Cosmetic Science Society, Vol. 30, No. 4, pp. 316-332

[Non-Patent Document 2] Hara, Y., "Development of New Evaluation Method Based on Characterization of Each Crow's Feet Wrinkle by Three-Dimensional Analysis," Journal of Japanese Cosmetic Science Society, Vol. 35, No. 2, pp. 93-98

SUMMARY OF THE INVENTION

Problems to be Solved by the Invention

The conventional techniques such as those described above, however, perform assessment and the like of so-called fixed wrinkles, and there have been no techniques or the like of analyzing or assessing expression wrinkles, which are believed to be the cause of fixed wrinkles.

Furthermore, normally, wrinkles change with expressions or a twist caused by pressing skin in one direction with a finger, and the amount of the change and the positions of wrinkles differ from person to person. Therefore, it is difficult to properly assess expression wrinkles or a twist from an image, so that it has been impossible to properly determine expression wrinkles or a twist or to analyze a skin condition from potential wrinkles or the like caused by a change in the expression or daily care.

An embodiment of the present invention has been made in view of the above-described, and has an object of providing an image analysis apparatus, an image analysis method, and an image analysis program for properly analyzing a skin condition from expression wrinkles of a subject or a twist of the skin at the time of care.

Means for Solving the Problems

In order to solve the above-described problems, an embodiment of the present invention adopts means for solving the problems having the following features.

According to an embodiment, an image analysis apparatus that analyzes a skin condition from a video of the face of a subject captured with an imaging part includes a tracking part configured to track the amount of changes of multiple tracking points arranged in advance in an analysis region of the face based on a change in the expression of the face included in the video, and obtain the compression ratio of the skin in the analysis region based on the amount of changes, and a skin condition analysis part configured to analyze the skin condition of the subject based on the compression ratio obtained by the tracking part.

Effects of the Invention

According to an embodiment of the present invention, it is possible to properly analyze a skin condition from expression wrinkles of a subject or a twist of the skin at the time of care.

BRIEF DESCRIPTION OF THE DRAWINGS

FIG. 4 is a flowchart illustrating an example of an image analysis process according to Example 1.

FIGS. 5A and 5B are diagrams for illustrating tracking points arranged in an analysis region.

FIG. 11 is a (second) diagram illustrating an analysis result according to Example 1.

FIGS. 12A through 12C are diagrams illustrating an analysis result according to Example 1.

FIG. 15 is a (first) diagram illustrating an analysis result according to Example 2.

FIG. 17 is a diagram illustrating an analysis result of forehead wrinkles.

FIGS. 19A through 19C are diagrams illustrating an analysis result according to Example 3.

EMBODIMENT OF THE INVENTION

Embodiment of the Present Invention

According to an embodiment of the present invention, in order to analyze a skin condition from dynamic wrinkles of a subject (for example, expression wrinkles such as laugh lines, anger lines or cry lines or a twist of skin at the time of care), an analysis region is specified by setting tracking points on a predetermined part of a face, wrinkle movements caused by a change in the expression are imaged using, for example, imaging means such as a high speed camera, and wrinkles are analyzed while tracking the imaging results in a time series.

Furthermore, according to an embodiment of the present invention, it is possible to calculate wrinkle parameters (such as the area, length, and ratio of a wrinkle) by extracting wrinkles from an extracted image using a preset wrinkle filter or the like. Furthermore, it is possible to create a stress map or the like by performing a strain analysis or a strain and stress analysis of the obtained image. As a result, it is possible to properly analyze and assess the skin condition of a subject. A description is given below, using drawings, of a preferred embodiment of an image analysis apparatus, an image analysis method, and an image analysis program according to the present invention.

Functional Configuration of Image Analysis Apparatus

Figure 1:
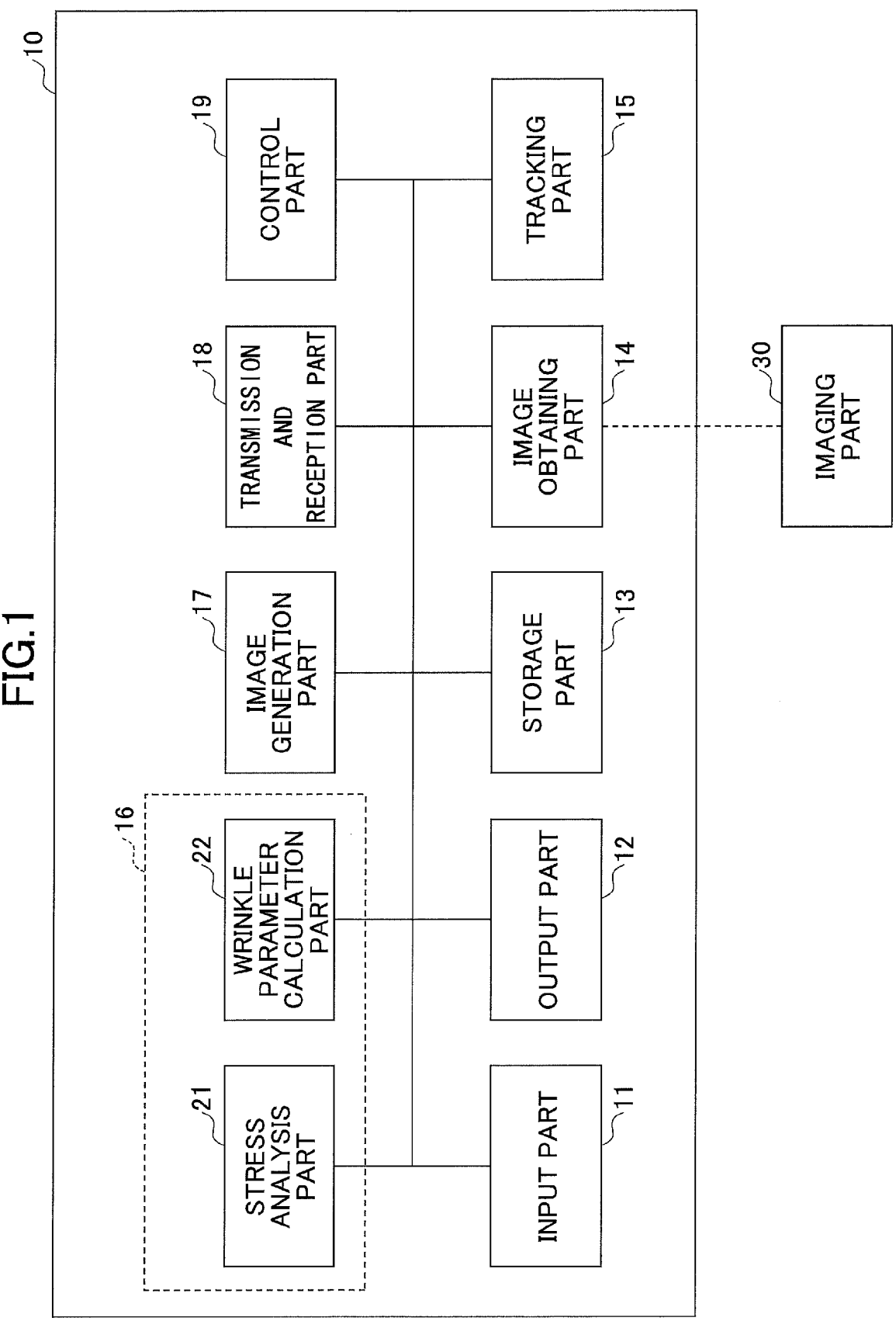
FIG. 1 is a diagram illustrating a functional configuration of an image analysis apparatus.

FIG. 1 is a diagram illustrating a functional configuration of an image analysis apparatus. An image analysis apparatus 10 illustrated in FIG. 1 includes an input part 11, an output part 12, a storage part 13, an image obtaining part 14, a tracking part 15, a skin condition analysis part 16, an image generation part 17, a transmission and reception part 18, and a control part 19. Furthermore, the skin condition analysis part 16 includes a stress analysis part 21 and a wrinkle parameter calculation part 21. The image analysis apparatus 10 illustrated in FIG. 1 is externally connected to an imaging part 30 as a non-limiting example, and the imaging part 30 may alternatively be installed in the image analysis apparatus 10.

The input part 11 receives inputs of various kinds of instructions from a user or the like of the image analysis apparatus 10. The input part 11 is implemented by, for example, a keyboard, a pointing device such as a mouse, etc.

The output part 12 displays and outputs the contents of an input made with the input part 11 and what is executed based on the contents of the input. The output part 12 is implemented by a display, a loudspeaker, etc. Furthermore, the output part 12 may have a function of a printer or the like, and in this case, may provide a user with the result of an image analysis or the like by printing the result on a printing medium such as paper.

The input part 11 and the output part 12 may be implemented by a one-piece input and output part such as a touchscreen panel. In this case, a user may make an input by touching a predetermined position on the screen using a finger or a stylus.

The storage part 13 stores various kinds of data necessary for an image analysis according to this embodiment. For example, the storage part 13 stores various kinds of data that may include, but are not limited to, captured images (time-series images and video) that the image obtaining part 14 obtains from the imaging part 30, the results of tracking by the tracking part 15, the results of analysis by the skin condition analysis part 16, and images by the image generation part 17.

The storage part 13 may also store, for example, settings information for performing an image analysis and various kinds of data (such as captured images) obtained from an external apparatus connected via a communication network through the transmission and reception part 18. Furthermore, it is possible to read various kinds of stored data from and perform writing to the storage part 13 as required.

The image obtaining part 14 obtains a face image of a subject captured with the externally connected imaging part 30. The face image may be an image of the entire frontal area of a face, an image of a profile, an image of the area of part of a face, or an image that is a combination of the above-described images.

Here, according to this embodiment, images that may be obtained by the image obtaining part 14 are, for example, time-series images including a preset analysis region, and are a video that includes multiple frame images. Furthermore, predetermined tracking points are arranged at predetermined intervals in the preset analysis region. Examples of the tracking points may include, but are not limited to, points and marks having a predetermined shape such as a triangle, a quadrangle or a star. The tracking points are provided on a skin surface that is a target of analysis with a color or the like that makes it possible to track their positions in performing predetermined image processing from image data.

Accordingly, the image obtaining part 14 obtains time-series images (video) that include the above-described tracking points from the imaging part 30. Furthermore, according to this embodiment, in order to analyze expression wrinkles, for example, a subject is caused to change from the state of a straight face (normal face) to a preset facial expression or from a preset facial expression to the state of a normal face in a time series. This change may be repeated. The imaging part 30 captures a video of a face of the expression that has changed.

Here, the imaging part 30 that is used may be, but is not limited to, for example, a high speed camera or the like that is capable of capturing a video at a frame rate higher than or equal to a video rate (30 fps). The high speed camera that is used to capture an image may be, but is not limited to, for example, "Microscope 'VW-6000'" manufactured by Keyence Corporation or the like. Furthermore, when obtaining a face image of the subject, as a non-limiting example, imaging by the imaging part 30 is preferably performed under, for example, such a lighting condition as to emphasize wrinkles of the face.

It is possible for the image obtaining part 14 to obtain a desired video (time-series images) by generating various kinds of camera parameters such as the above-described imaging range (for example, an angle of view, focus, etc.)

and lighting condition, an imaging condition (a time interval between frames), and resolution, and outputting the generated parameters to the imaging part 30. Furthermore, the image obtaining part 14 may store a video obtained from the imaging part 30 in the storage part 13 or directly output the video to the tracking part 15.

The tracking part 15 tracks a skin movement in the analysis region using a video stored in the storage part 13, a video obtained from the image obtaining part 14, a video obtained from an external apparatus through the transmission and reception part 18, or the like. As a non-limiting example, the tracking of the analysis region obtains the movement of one or more of the above-described tracking points (marks) included in the time-series images. Furthermore, the tracking part 15 obtains the compression ratio of the skin of the subject based on the amounts of change of the travel distances of the tracking points in the time series of face images. The compression ratio is, but is not limited to, the amount of change (the degree of contraction) of the travel, distance of each tracked point. Furthermore, the tracking part 15 may obtain, as an example of the compression ratio, the amount of strain from a change in the distance between tracked points. The amount of strain is, but is not limited to, for example, the amount of compression or tension of a surface area surrounded by points due to a change in the expression.

The skin condition analysis part 16 analyzes a skin condition based on the above-described time-series movements (such as the compression ratio) of tracking points. The analysis of a skin condition refers to, for example, analyzing expression wrinkles and, based on its result, analyzing a stress on the skin or calculating wrinkle parameters or the like for expressing expression wrinkles in numerical values. The analysis of a skin condition, however, is not limited to this, and for example, a twist of skin due to pressing with a finger at the time of care may be analyzed.

For example, the stress analysis part 21 in the skin condition analysis part 16 identifies a heavily stressed area in the analysis region from the amount of strain that corresponds to a change in the expression obtained from the point group data of multiple tracking points, or the like. Furthermore, the stress analysis part 21 performs a skin mechanics measurement that quantifies the flexibility (hardness) and the like of skin, and analyzes strain as stress using its result. The skin mechanics measurement refers to, but is not limited to, for example, measuring the time of propagation of a shock wave between two points on the skin, and based on its result, quantifies the flexibility, the condition and direction of elasticity, etc., of the skin.

The wrinkle parameter calculation part 22 in the skin condition analysis part 16 classifies wrinkles in the analysis region into one or more preset types of wrinkles based on tracking points arranged in the region. Furthermore, the skin condition analysis part 16 performs noise processing on wrinkles recognized in an image, and deletes wrinkles if the wrinkles are not present in the preceding and succeeding images in the video.

Furthermore, the wrinkle parameter calculation part 22 calculates parameters with respect to the wrinkles obtained by the above-described process. The wrinkle parameters include, but are not limited to, at least one of a wrinkle area, a wrinkle length, a wrinkle ratio, etc.

The image generation part 17 generates an image to be displayed on the screen of the output part 12 or the like based on the above-described analysis results obtained by the skin condition analysis part 16.

As a non-limiting example, the image generation part 17 generates an image, a stress map, or the like in which the stressed area obtained by the stress analysis part 21 is highlighted, generates an image in which the parameters calculated by the wrinkle parameter calculation part 22 are indicated, and generates an image in which a wrinkled area of a face due to a change in the expression is highlighted. For example, the image generation part 17 may generate, for example, a settings screen for inputting various kinds of settings information for performing an image analysis according to this embodiment by a user, or the like.

When displaying the generated image on the screen of the output part 12, the image generation part 17 may also, for example, enlarge and display a predetermined region or display the predetermined region after performing processing such as luminance inversion so as to make the image easily viewable to a user or a subject.

Furthermore, the image generation part 17 may generate a video by generating the above-described image in which wrinkles or a stress is expressed for each frame of the video. It is possible for a user to more properly understand changes in wrinkles or a stress due to changes in the expression by viewing this video. As a result, it is possible to properly evaluate a skin condition.

The transmission and reception part 18 is a communication part for transmitting data to and receiving data from an external apparatus or the like connected via a communication network typified by, for example, the Internet, a IAN (Local Area Network), or the like. The transmission and reception part 18 may receive face image data, subject information, processing programs, etc., already stored in the external apparatus and may also transmit the results of analysis by the image analysis apparatus 10 to the external apparatus via the communication network.

The control part 19 controls all the components of the image analysis apparatus 10. Specifically, the control part 19 performs control operations such as causing the image obtaining part 14 to obtain an image based on a user's instruction or the like through the input part 11, causing the skin condition analysis part 16 to analyze a skin condition, and causing the image generation part 17 to generate an image, but the control operations are not limited to these.

Examples of the image analysis apparatus 10 may include, but are not limited to, a personal computer (PC), a server, a communication terminal such as a tablet terminal or a smartphone, and a game apparatus.

[Hardware Configuration of Image Analysis Apparatus 10]

Figure 2:
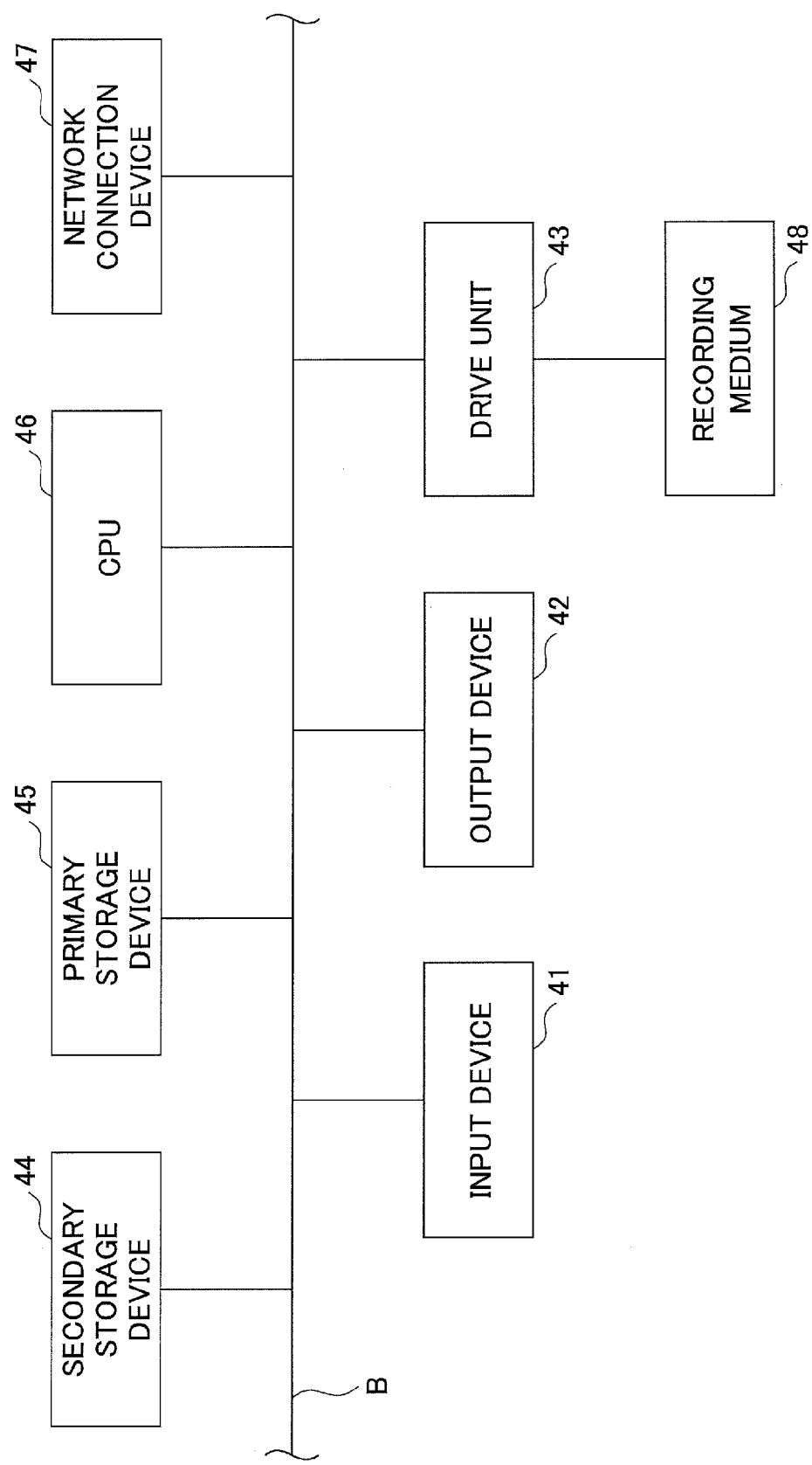
FIG. 2 is a diagram illustrating a hardware configuration of the image analysis apparatus.

FIG. 2 is a diagram illustrating a hardware configuration of an image analysis apparatus. The image analysis apparatus 10 according to FIG. 2 includes an input device 41, an output device 42, a drive unit 43, a secondary storage device 44, a primary storage device 45, a CPU (Central Processing Unit) 46 that performs various kinds of control, and a network connection device 47, which are interconnected by a system bus B.

The input device 41 includes a keyboard and a pointing device such as a mouse operated by a user or the like and a voice input device such as a microphone, and receives inputs of instructions to execute a program, various kinds of operation information, information for activating software or the like from a user or the like, etc.

The output device 42 includes a display that displays various kinds of windows and data necessary for operating the image analysis apparatus 10, etc., and displays the progress and result of execution of a program using a control program of the CPU 46.

Here, according to this embodiment, an execution program installed in a computer serving as the image analysis apparatus is provided by way of, for example, a portable recording medium 48 such as a USB (Universal Serial Bus) memory, a CD-ROM or a DVD. The recording medium 48 in which the program is recorded may be loaded into the drive unit 43. The execution program contained in the recording medium 48 is installed in the secondary storage device 44 from the recording medium 48 through the drive unit 43 based on a control signal from the CPU 46.

The secondary storage device 44 is a storage part or the like such as a hard disk drive or an SSD (Solid State Drive). The execution program according to this embodiment, a control program or the like provided in the computer, etc., may be stored in and be input to and output from the secondary storage device 44 as required based on a control signal, from the CPU 46. Necessary information may be read from the information stored in the secondary storage device 44 or written to the secondary storage device 44 based on a control signal from the CPU 46.

The primary storage device 45 stores the execution program read from the secondary storage device 44 by the CPU 46, and the like. The primary storage device 45 includes a RO (Read Only Memory) and a RAM (Random Access Memory). The secondary storage device 44 and the primary storage device 45 correspond to, for example, the above-described storage part 13.

The CPU 46 is capable of implementing processes by controlling the processes of the entire image analysis apparatus 10, such as various kinds of operations and the inputting of data to and the outputting of data from hardware components, based on a control program such as an operating system and the execution program stored in the primary storage device 45. Various kinds of information and the like required during execution of a program may be obtained from the secondary storage device 44, and the results of execution and the like may be stored in the secondary storage device 44.

Specifically, for example, by causing the secondary storage device 44 to execute an installed program based on an instruction to execute the program or the like obtained from the input device 41, the CPU 46 executes a process corresponding to the program in the primary storage device 45. For example, by causing an image analysis program according to this embodiment to be executed, the CPU 46 executes processes such as the above-described obtaining of an image by the image obtaining part 14, tracking of tracking points by the tracking part 15, analysis of a skin condition by the skin condition analysis part 16, and generation of an image by the image generation part 17. The contents of processes in the CPU 46 are not limited to these. The contents of execution by the CPU 46 may be stored in the secondary storage device 44 as required.

The network connection device 47 obtains the execution program, software, settings information, etc., from an external apparatus or the like connected to a communication network by connecting to the communication network based on a control signal from the CPU 46. Furthermore, the network connection device 47 is capable of providing an external apparatus or the like with the results of execution obtained by executing a program or the execution program itself according to this embodiment.

It is possible to execute an image analysis process according to this embodiment through the hardware configuration as described above. Furthermore, the image analysis process according to this embodiment may be implemented by installing the execution program (image analysis program) that enables a computer to execute the above-described functions in, for example, a general-purpose PC, a communication terminal such as a smartphone, a game apparatus, or the like.

[Example Process of Image Analysis Apparatus 10]

Figure 3:
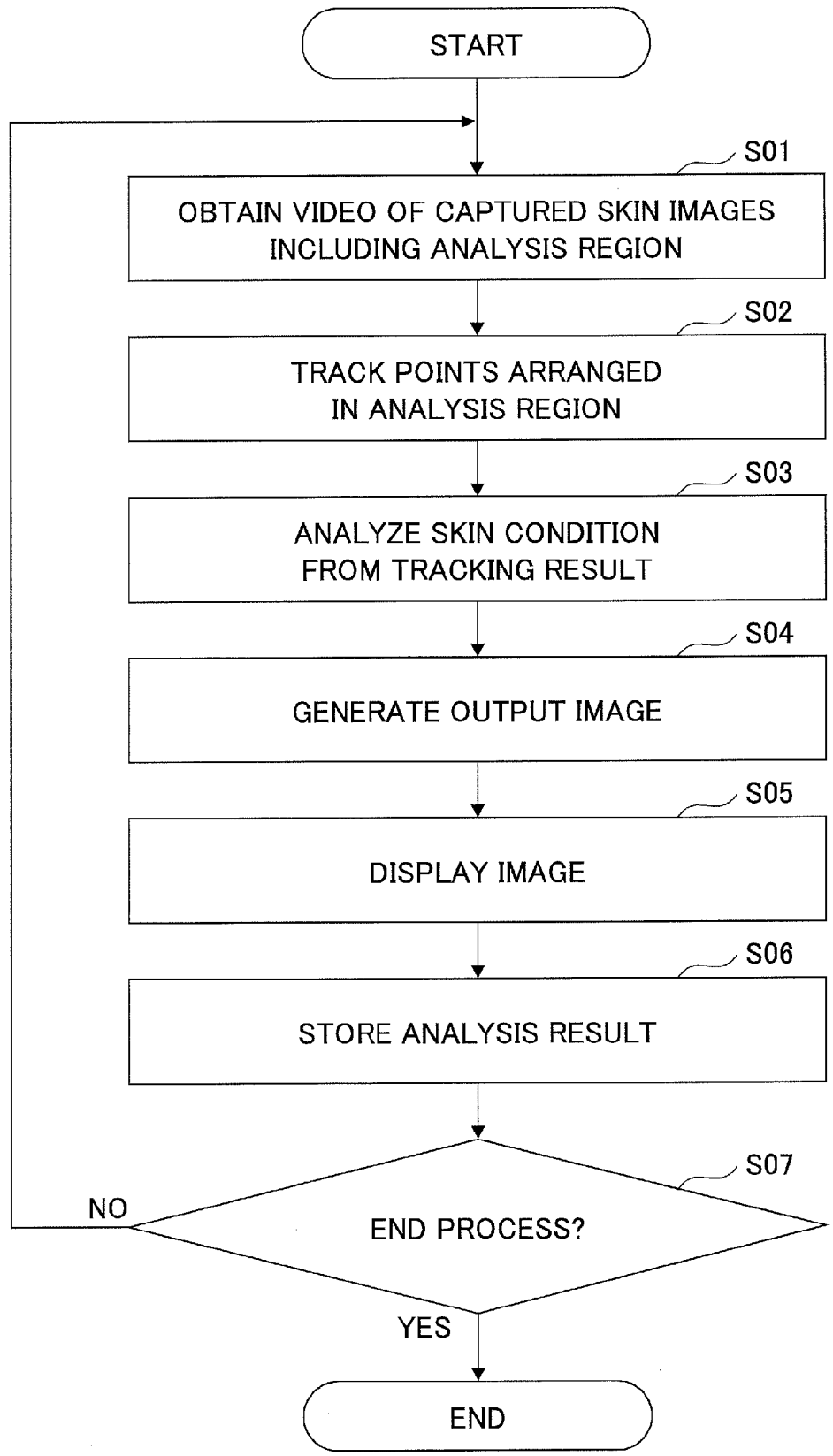
FIG. 3 is a flowchart illustrating a process of the image analysis apparatus according to this embodiment.

Here, a description is given, using a flowchart, of a process of the image analysis apparatus 10 according to this embodiment. FIG. 3 is a flowchart illustrating a process of an image analysis apparatus according to this embodiment.

In the case of FIG. 3, the image obtaining part 14 of the image analysis apparatus 10 obtains a video of captured skin images including an analysis region (S01). As a non-limiting example, a video to be captured is preferably captured with a high speed camera.

Next, the tracking part 15 of the image analysis apparatus 10 tracks points arranged in the analysis region with respect to the video obtained in the process of S01 (S02). The points refer to tracking points (marks) provided in the analysis region of the face of a subject in advance. According to this embodiment, for example, multiple points are arranged in the region at predetermined intervals.

Next, the skin condition analysis part 16 of the image analysis apparatus 10 analyzes a skin condition from the tracking result (S03). The process of S03 may be, but is not limited to, for example, analysis of a stress on the skin, calculation of wrinkle parameters, their combination, or the like.

Next, the image generation part 17 of the image analysis apparatus 10 generates an image based on the skin analysis result obtained in the process of S03 (S04), and causes the generated image to be displayed on the screen of the output part 12 or the like (S05). In the process of S05, the image generation part 17 may cause the generated image to be displayed on the screen of an external apparatus connected by a communication network or the like. Furthermore, in the processes of S04 and S05, a video in which images are arranged in a time series may be generated, and the generated video may be displayed on the output part 12 or the like.

The storage part 13 of the image analysis apparatus 10 stores the skin analysis result obtained in the process of S03, and the like (S06). Here, the image analysis apparatus 10 determines whether to end the image analysis process (S07), and returns to the process of S01 if the process is not to be ended (NO at S07). On the other hand, if the process is to be ended based on a user's instruction or the like (YES at S07), the image analysis apparatus 10 ends the image analysis process.

[Skin Condition Analysis Process: Example 1 (Stress Analysis)]

Next, a description is given of Example 1 of the above-described skin condition analysis process in the skin condition analysis part 16. In Example 1, a description is given of a stress analysis based on expression wrinkles. In the following description, laugh lines are used as an example of expression wrinkles, while expression wrinkles are not limited to these and may be, for example, anger lines, cry lines, or the like.

According to Example 1, for example, more than or equal to one hundred tracking points (marks) preset in the analysis region of the face of a subject are put at the outer corner of an eye at intervals of 1 mm. It is possible to directly attach the above-described points to the skin, while it is possible to easily provide tracking points using a stamp or the like for putting points at the above-described position in advance.

Furthermore, according to Example 1, points are put at the outer corner of the eye using a stamp, and a skin movement at the outer corner of the eye at the time when the subject laughs is imaged with a high speed camera. Furthermore, according to Example 1, a two-dimensional strain is obtained from a change in the distance between tracking points, and the obtained strain is displayed. Furthermore, according to Example 1, a skin mechanics measurement that quantifies the flexibility (hardness) and the like of skin is performed, and by taking its result into consideration, the strain is displayed as a stress and an analysis is performed. As a non-limiting example, the skin mechanics measurement may employ, for example, "shock wave measurement apparatus 'Reviscometer (registered trademark)'" (Courage+Khazaka electronic GmbH).

FIG. 4 is a flowchart illustrating an example of the image analysis process according to Example 1. In the case of FIG. 4, tracking points arranged at predetermined intervals in an analysis region in which the skin condition of a subject is to be analyzed are put at the outer corner of an eye using a stamp or the like made in advance. In view of, for example, a load on the skin, easiness in selecting a color that is easily distinguishable from the skin, etc., it is preferable to use a predetermined cosmetic such as mascara or eyeliner rather than ink or the like in putting points. As a non-limiting example, with respect to the number of points put in the region, more than or equal to one hundred points are preferably arranged at equal intervals in the analysis region.

FIGS. 5A and 5B are diagrams for illustrating tracking points arranged in the analysis region. FIG. 5A illustrates an example of arranged tracking points, and FIG. 5B illustrates an analysis region including a point group of tracking points. In the case illustrated in FIG. 5A, 121 tracking points (marks) 51 in an 11 by 11 matrix are indicated at predetermined intervals on an image 50 of the vicinity of the outer corner of the right eye of a subject. Furthermore, as illustrated in FIG. 5B, the tracking points are provided in an arrangement in an analysis region 52.

According to this embodiment, an area where the tracking points 51 are arranged at predetermined intervals may be caused to become the analysis region 52. Therefore, for example, a region smaller than the region illustrated in FIG. 5B (for example, the right half, the left half, or the like of the analysis region 52 illustrated in FIG. 5B) may be rendered a target of analysis. Furthermore, a partial region inside the region surrounded by tracking points may be rendered the analysis region 52.

According to Example 1, information on a stress on the skin due to a change in expression wrinkles is analyzed by tracking how the tracking points 51 move when a straight face (normal face) changes to a laughing face or when a laughing face changes to a straight face.

In the case of FIG. 4, the stress analysis part 21 obtains a video of laughing lines of a subject (S11). In the process of S11, as a non-limiting example, a video captured with a high speed camera with adjustment to a lighting condition that emphasizes wrinkles and without becoming a blurred image is preferably obtained. Furthermore, in the process of S11, the subject is asked to have a full smile from a straight face, and a video of captured images of a change in the skin including the analysis region (the vicinity of the outer corner of the eye) at that time is obtained.

Next, the stress analysis part 21 performs an analysis by performing the tracking of tracking points based on, for example, PIV (Particle Image Velocimetry) or the like (S12). PIV is a technique to measure a velocity field using pattern matching or the like from, for example, particle images captured at different times, and is a method to measure the velocity and displacement of particles from digital images or the like.

As a non-limiting example, "two-dimensional video measurement software 'Move-tr/2D'" of Library Co., Ltd. or the like may be used for the tracking of tracking points based on PIV, while other software may also be used.

The stress analysis part 21 may store the positions of tracking points in each scene (frame) of the video in the storage part 13 in the form of a csv file, a txt file, or the like based on the analysis by tracking. Furthermore, the stress analysis part 21 may also perform image processing to decompose a video (for example, an avi file) into successive still images (for example, a bmp file).

Next, the stress analysis part 21 obtains changes in the distances between tracking points in the analysis region, and performs a strain analysis from the amount of the changes (S13). As a non-limiting example, "strain measurement software 'Strain-mp'" of Library Co., Ltd. or the like may be used for the strain analysis, while other software may also be used.

Next, the stress analysis part 21 performs the above-described skin mechanics measurement in the analysis region, and obtains stress information based on the skin mechanics measurement value and the strain analysis result obtained by the process of S13 (S14). In the process of S14, information on the stress due to laugh lines is obtained by, for example, multiplying the hardness of the skin obtained by the skin mechanics measurement by the strain analysis result. Specifically, as a non-limiting example, "Stress=E (hardness)×Strain." According to Example 1, when the stress information is obtained by the stress analysis part 21, the image generation part 17 may generate and display a stress map or the like in which a heavily stressed area of the skin is visualized using the stress information.

[About PIV]

Here, PIV according to this embodiment is specifically described. In the following description, PTV (Particle Tracking Velocimetry), which is an example of PIV, is used as a non-limiting example.

According to PTV of Example 1, locations (tracking points) to which points are put by causing a cosmetic or the like to adhere in the analysis region are determined as targets of tracking in the image, and the features (for example, color, shape and size) and the like of the tracking points are determined as initial settings. At this point, features of the targets of tracking that do not overlap those of an area around the targets of tracking as much as possible are extracted based on luminance values, RGB values or the like, and the features of the targets of tracking may be automatically determined based on their numbers of pixels (check region size), centroids, etc. Furthermore, according to Example 1, the area to be tracked in the image (analysis region size) is determined.

Next, a captured video is analyzed based on the determined settings. Here, F(t−1) is defined as the image of a frame in which the X and Y values of the target of tracking (tracking points) are determined, and F(t) is defined as the image of the frame next to F(t−1) in which the X and Y values of the target of tracking are not determined. At this point, in the image of F(t), the coefficient of correlation with a target of tracking is calculated with respect to the entire analysis region size around the X and Y values of the target of tracking in F(t−1), and X and Y values that show the highest correlation value are determined as the X and Y values of the target of tracking in F(t).

[About Strain Analysis]

Next, the above-described strain analysis is specifically described. According to Example 1, a video of the movement of the skin on which tracking points are put is captured using a high speed camera. The tracking points are tracked according to PTV with respect to each of the frames of the video, and for example, the degree of the deformation of the analysis region surrounded by the put points (for example, a quadrangle) from the preset initial frame (initial position) is calculated as a strain value. As a non-limiting example, the value of a compressive strain is positive (plus) in the case of compression.

Next, a description is given of a method of calculating strain.

[Strain Calculation Example 1]

According to Strain Calculation Example 1, with respect to displacements u and v, plane strain is given by Eq. (1) shown below:

$$\epsilon_x = -\partial u/\partial x, \epsilon_y = -\partial v/\partial y, \gamma_{xy} = -(\partial u/\partial y + \partial v/\partial x) \text{(compression is positive)} \quad (1)$$

where x and y indicate plane coordinates.

At this point, principal strain may be calculated by Eqs. (2) through (4) shown below:

$$\varepsilon_1 = \frac{\varepsilon_x + \varepsilon_y}{2} + \sqrt{\left(\frac{\varepsilon_x - \varepsilon_y}{2}\right)^2 + (\gamma_{xy})^2} \quad (2)$$

$$\varepsilon_2 = \frac{\varepsilon_x - \varepsilon_y}{2} + \sqrt{\left(\frac{\varepsilon_x - \varepsilon_y}{2}\right)^2 + (\gamma_{xy})^2} \quad (3)$$

$$\gamma_{max} = \varepsilon_1 - \varepsilon_2 \quad (4)$$

[Strain Calculation Example 2]

According to Strain Calculation Example 2, the area of a quadrangle that is an example of the analysis region is determined using a cross product, and a strain value is calculated from the ratio of areas before and after a change in the expression. Here, FIG. 6 is a diagram for illustrating Strain Calculation Example 2.

Figure 6:
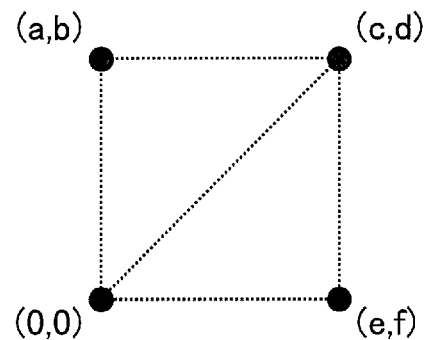
FIG. 6 is a diagram for illustrating a strain calculation example 2.

In the case of FIG. 6, when the analysis region is a quadrangle, letting the x and y coordinates of the vertices of the quadrangle be (0, 0), (a, b), (c, d) and (e, f), the area of the quadrangle is given by "Area=½×((√(a×d−b×c)²)+(√(c×f−d×e)²))."

Based on the above-described calculation, the strain value may be calculated as "Strain value=(the quadrangular area of a frame at the time of the deformation of the expression that is determined as a target)/(the initial quadrangular area of the frame (of a straight face))."

[Strain Calculation Example 3]

Figure 7:
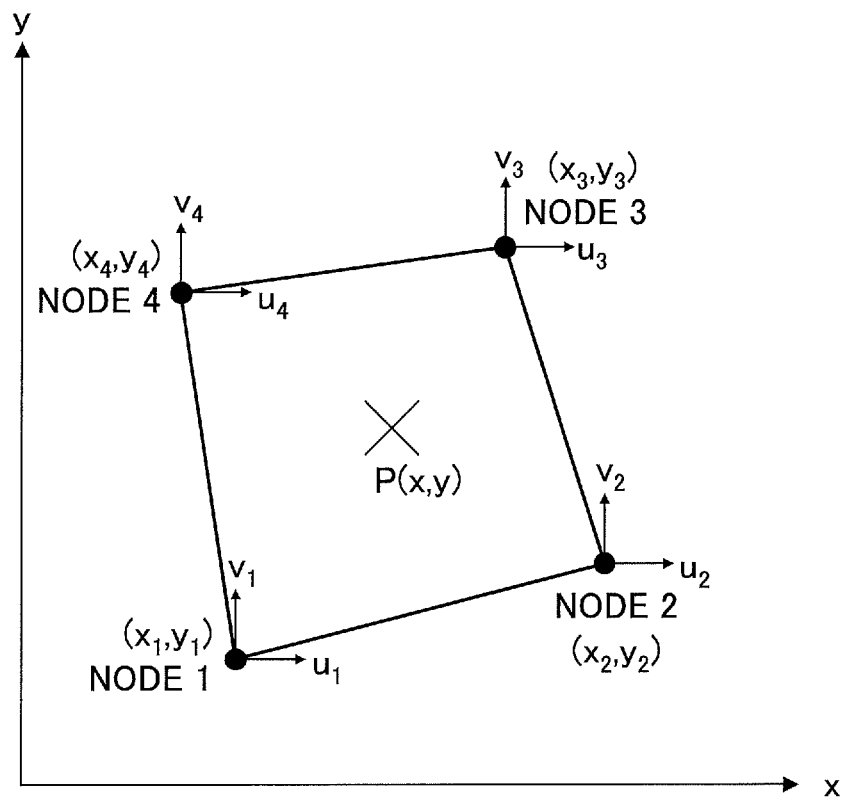
FIG. 7 is a diagram for illustrating a strain calculation example 3.

According to Strain Calculation Example 3, the strain of a centroid P ($\epsilon_x$, $\epsilon_y$) is calculated. FIG. 7 is a diagram for illustrating Strain Calculation Example 3.

Here, letting the initial coordinates of the vertices of a quadrangle are be (x1, y1), (x2, y2), (x3, y3) and (x4, y4) and letting the displacements of Nodes 1 through 4 be (u1, v1), (u2, v2), (u3, v3) and (u4, v4) as illustrated in FIG. 7, the strain of the centroid P may be calculated by Eqs. (5) and (6) shown below:

$$\varepsilon_x = \ln\left\{1 + \frac{(y_2 - y_4)u_1 + (y_3 - y_1)u_2 + (y_4 - y_2)u_3 + (y_1 - y_3)u_4}{(x_1 - x_3)(y_2 - y_4) - (y_2 - y_4)(y_1 - y_3)}\right\} \quad (5)$$

$$\varepsilon_y = \ln\left\{1 + \frac{(x_4 - x_2)v_1 + (x_1 - x_3)v_2 + (x_2 - x_4)v_3 + (x_3 - x_1)v_4}{(x_1 - x_3)(y_2 - y_4) - (y_2 - y_4)(y_1 - y_3)}\right\} \quad (6)$$

[Strain Calculation Example 4]

Figure 8A:
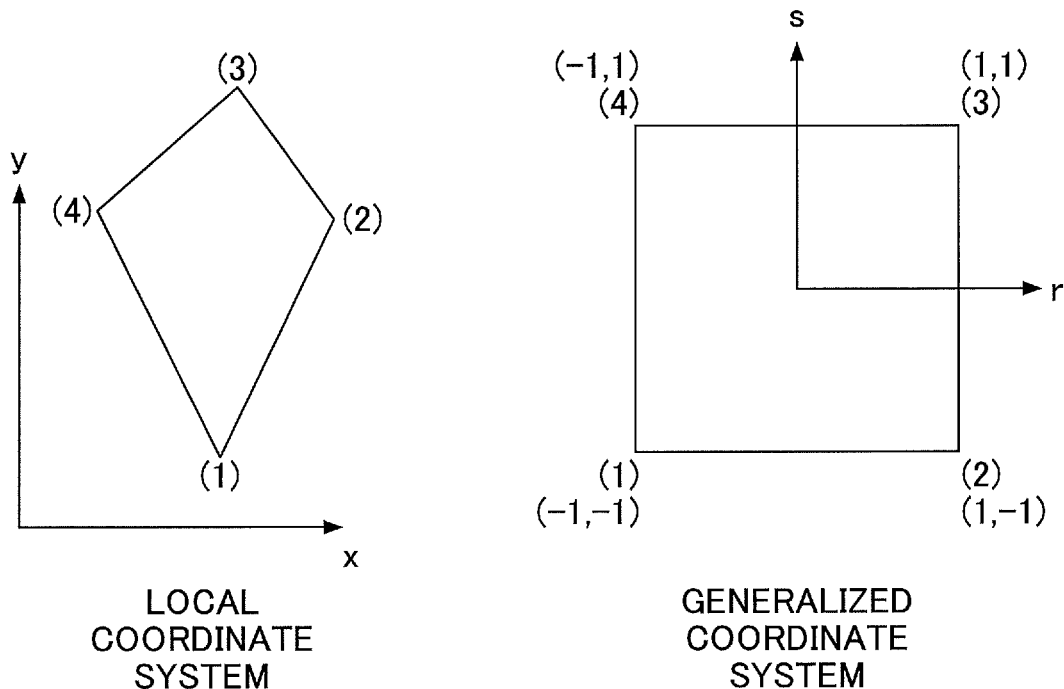
FIGS. 8A and 8B are diagrams for illustrating a strain calculation example 4.
Figure 8B:
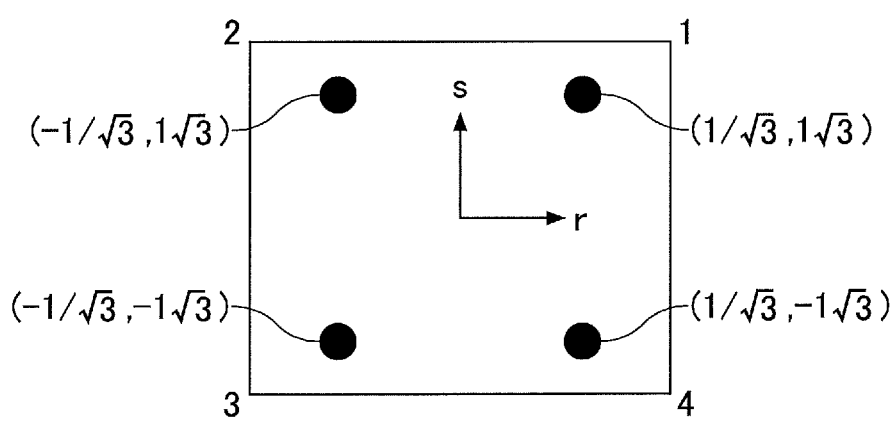

FIGS. 8A and 8B are diagrams for illustrating Strain Calculation Example 4. According to Strain Calculation Example 4, for example, as illustrated in FIG. 8A, a local coordinate system (a physical coordinate system) is converted into a generalized coordinate system (a natural coordinate system). Here, the four vertices (1) through (4) of a quadrangle are caused to correspond to (−1, −1), (1, −1), (1, 1) and (−1, 1), respectively. That is, a quadrangle of a local coordinate system is mapped to a square of a generalized coordinate system.

Here, a shape function (a displacement interpolation function) is defined as Eq. (7) shown below:

$$H = \{h_1, h_2, h_3, h_4\} = \quad (7)$$
$$\left\{\frac{1}{4}(1-r)(1-s), \frac{1}{4}(1+r)(1-s), \frac{1}{4}(1+r)(1+s), \frac{1}{4}(1-r)(1+s)\right\}$$

The strain in the generalized coordinate system illustrated in FIG. 8A becomes the derivative of the partial differential of the displacement interpolation function as Eq. (8) shown below, which is expanded to Eq. (9):

$$\frac{\partial u}{\partial r} = \sum_{i=1}^{4} \frac{\partial h_i}{\partial r} u_i, \quad \frac{\partial u}{\partial s} = \sum_{i=1}^{4} \frac{\partial h_i}{\partial s} u_i \quad (8)$$

$$\begin{Bmatrix} \frac{\partial u}{\partial r} \\ \frac{\partial u}{\partial s} \end{Bmatrix} = \frac{1}{4}\begin{bmatrix} -(1-s) & (1-s) & (1+s) & -(1+s) \\ -(1-r) & -(1+r) & (1+r) & (1-r) \end{bmatrix} \begin{Bmatrix} u_1 \\ u_2 \\ u_3 \\ u_4 \end{Bmatrix} \quad (9)$$

In a plane problem, the variation relationship between a generalized coordinate system and a local coordinate system is Eq. (10) shown below:

$$\begin{Bmatrix} \frac{\partial}{\partial r} \\ \frac{\partial}{\partial s} \end{Bmatrix} = \quad (10)$$

$$J \begin{Bmatrix} \frac{\partial}{\partial x} \\ \frac{\partial}{\partial y} \end{Bmatrix} = \begin{bmatrix} \frac{\partial x}{\partial r} & \frac{\partial y}{\partial r} \\ \frac{\partial x}{\partial s} & \frac{\partial y}{\partial s} \end{bmatrix} \begin{Bmatrix} \frac{\partial}{\partial x} \\ \frac{\partial}{\partial y} \end{Bmatrix} = \sum_{i=1}^{4} \begin{bmatrix} \frac{\partial h_i}{\partial r} x_i & \frac{\partial h_i}{\partial r} y_i \\ \frac{\partial h_i}{\partial s} x_i & \frac{\partial h_i}{\partial s} y_i \end{bmatrix} \begin{Bmatrix} \frac{\partial}{\partial x} \\ \frac{\partial}{\partial y} \end{Bmatrix}$$

In Eq. (10) described above, J indicates the Jacobian matrix. Accordingly, the inverse matrix of the Jacobian matrix is Eq. (11) shown below:

$$J^{-1} = \frac{1}{\det J}\begin{bmatrix} \frac{\partial y}{\partial r} & -\frac{\partial y}{\partial r} \\ -\frac{\partial x}{\partial s} & \frac{\partial x}{\partial s} \end{bmatrix} \quad (11)$$

Here, letting the strain be $\epsilon$, letting the strain-displacement conversion matrix (linear) (also referred to as the [B] matrix) be B, and letting u be a displacement vector in an element end face, the strain-displacement relational expression is defined as "$\epsilon = Bu$." The strain $\epsilon$ at this point may be expressed by Eq. (12) shown below:

$$\varepsilon = \left\{ \begin{array}{c} \varepsilon_x \\ \varepsilon_y \\ \gamma_{xy} \end{array} \right\} = \left\{ \begin{array}{c} \partial u / \partial x \\ \partial v / \partial y \\ \partial u / \partial y + \partial v / \partial x \end{array} \right\} \qquad (12)$$

The strain-displacement conversion matrix ([B] matrix) of a point i is calculated by Eq. (13) shown below (the [B] matrix exists for each point):

$$B_i = J_i^{-1} \times \begin{bmatrix} -(1-s_i) & 0 & (1-s_i) & 0 & 1+s_i & 0 & -(1+s_i) & 0 \\ 0 & -(1-r_i) & 0 & -(1+r_i) & 0 & 1+r_i & 0 & (1-r_i) \\ -(1-r_i) & -(1-s_i) & -(1+r_i) & (1-s_i) & 1+r_i & 1+s_i & (1-r_i) & -(1+s_i) \end{bmatrix} \qquad (13)$$

Here, in creating a matrix, it is necessary to calculate an area integral. Unless the element is so simple in shape, however, the form of the integrand becomes complicated, so that it is almost impossible to analytically integrate. Therefore, according to Strain Calculation Example 4, for example, the Gaussian integral is employed.

The Gaussian integral is one method of numerically determining an integral based on the nature of the Lagrange polynomial by approximating an integrand with the Lagrange polynomial. In a quadrangular element (Nodes 1 through 4) according to this embodiment, Gaussian integral points (sampling points) for ensuring sufficient accuracy may be, for example, four with reference to the coordinate values $(r_i, s_i)$ as illustrated in FIG. 8B, which are, for example, 2×2=4 points of $r=\pm 1/\sqrt{3}$ and $s=\pm 1/\sqrt{3}$. In this case, the weight is W1=W2=1. At this point, the strain $\varepsilon$ may be calculated by Eq. (14) shown below:

$$\varepsilon = \left\{ \begin{array}{c} \varepsilon_x \\ \varepsilon_y \\ \gamma_{xy} \end{array} \right\} = \frac{1}{4} \sum_{i=1}^{4} B_i \left\{ \begin{array}{c} u_1 \\ v_1 \\ u_2 \\ v_2 \\ u_3 \\ v_3 \\ u_4 \\ v_4 \end{array} \right\} \qquad (14)$$

According to Strain Calculation Examples 1 through 4 described above, a preset method may be used for calculation, or two or more of the above-described calculation examples may be used in combination.

[Examples of Obtaining of Stress Information σ]

Figure 9A:
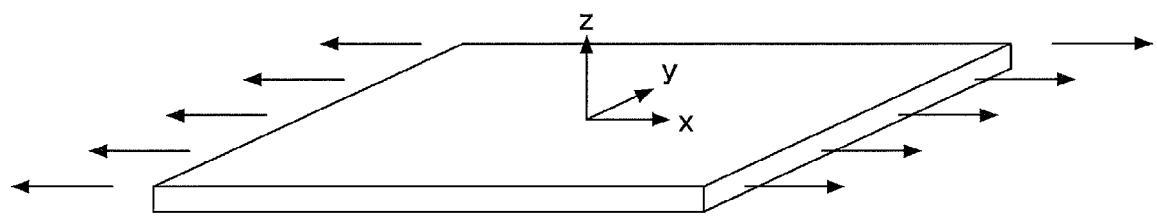
FIGS. 9A and 9B are diagrams for illustrating examples of obtaining of stress information.
Figure 9B:
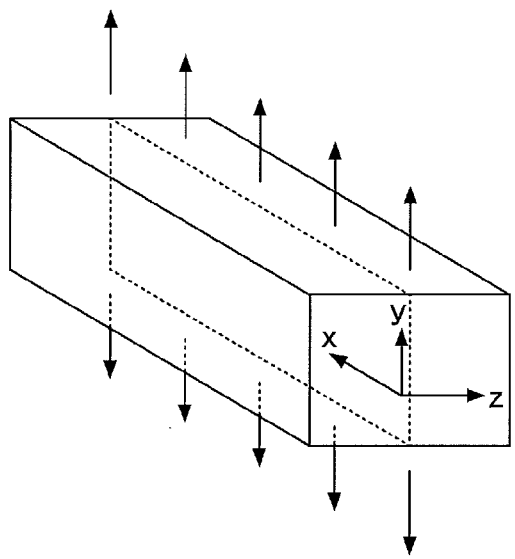

Next, calculation examples of stress information σ are specifically described. The stress information σ may be obtained by, for example, being displayed in a pseudo manner by assuming a plane stress condition or a plane strain. Here, FIGS. 9A and 9B are diagrams for illustrating examples of the obtaining of stress information. FIG. 9A illustrates a plane stress condition, and FIG. 9B illustrates a plane strain condition.

For example, when a plane stress condition (zero stress in the z direction) is assumed, it is possible to consider the case of a thin plate as illustrated in FIG. 9A. In this case, letting $\sigma_z$ be 0, letting $\gamma_{zx}$ be 0, and letting $\gamma_{yz}$ be 0, $\varepsilon$ is calculated by Eq. (15) shown below:

$$\varepsilon = \left\{ \begin{array}{c} \sigma_x \\ \sigma_y \\ \gamma_{xy} \end{array} \right\} = \frac{E}{1-v^2} \begin{bmatrix} 1 & v & 0 \\ v & 1 & 0 \\ 0 & 0 & \frac{1-v}{2} \end{bmatrix} \left\{ \begin{array}{c} \varepsilon_x \\ \varepsilon_y \\ \gamma_{xy} \end{array} \right\} \qquad (15)$$

In Eq. (15) described above, v indicates Poisson's ratio and E indicates Young's modulus. Furthermore, according to this embodiment, for example, 0.4 is employed as Poisson's ratio v. This is because Poisson's ratio is believed to be approximately 0.5 to approximately 0.4 for high water content biological objects because of their high incompressibility. Furthermore, Young's modulus E is estimated with the reciprocal of the skin mechanics measurement value obtained from a Reviscometer or the like, for example.

In the plane stress condition illustrated in FIG. 9A, the strain in the z direction is not zero, so that "$\varepsilon z = -v(\sigma x + \sigma y)/E$" holds.

Furthermore, when a plane strain condition (zero strain in the z direction) is assumed, it is possible to consider a cross section of a thick structure as illustrated in FIG. 9B. In this case, letting $\sigma_z$ be 0, letting $\gamma_{zx}$ be 0, and letting $\gamma_{yz}$ be 0, $\varepsilon$ is calculated by Eq. (16) shown below:

$$\varepsilon = \left\{ \begin{array}{c} \sigma_x \\ \sigma_y \\ \gamma_{xy} \end{array} \right\} = \frac{E(1-v)}{(1+v)(1-2v)} \begin{bmatrix} 1 & \frac{v}{1-v} & 0 \\ \frac{v}{1-v} & 1 & 0 \\ 0 & 0 & \frac{1-2v}{2(1-v)} \end{bmatrix} \left\{ \begin{array}{c} \varepsilon_x \\ \varepsilon_y \\ \gamma_{xy} \end{array} \right\} \qquad (16)$$

Here, the stress in the z direction is not zero, "$\sigma z = vE(\varepsilon x + \varepsilon y)/((1+v)(1-2v))$" holds.

In the above-described examples, for simplification, v and $\varepsilon$ described above may be considered to be sufficiently small, so that $\sigma = \varepsilon E$ may be substituted. Accordingly, in the above-described examples, σ also can output a principal stress the same as $\varepsilon$.

[Examples of Analysis Result in Example 1]

Figure 10:
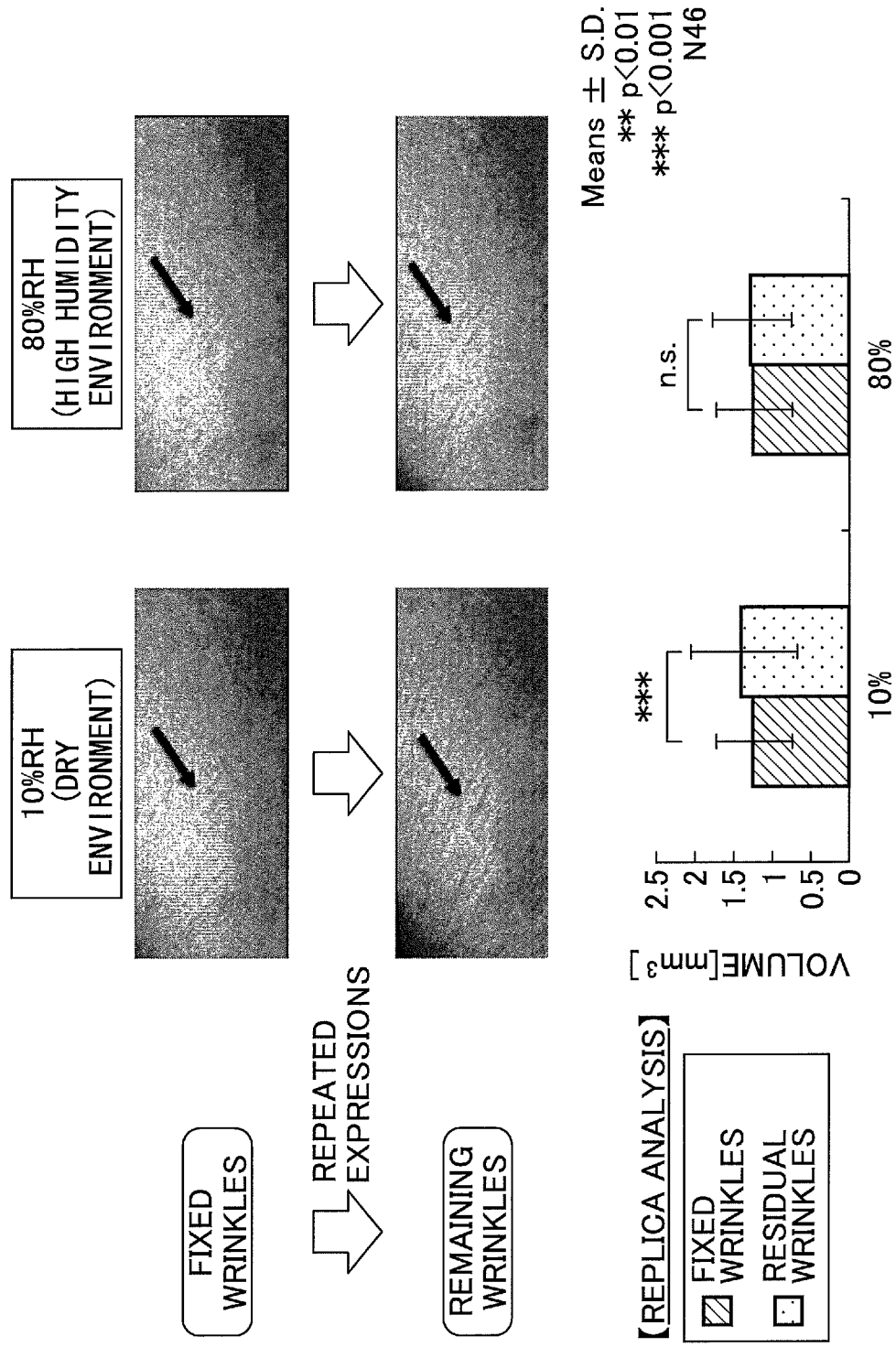
FIG. 10 is a (first) diagram illustrating an analysis result according to Example 1.

Here, FIG. 10, FIG. 11 and FIGS. 12A through 12C are (first through third) diagrams illustrating analysis results according to Example 1. In the example of FIG. 10, the condition of fixed wrinkles and residual wrinkles obtained by repeating changing the expression multiple times is illustrated. Furthermore, in the example of FIG. 10, the results in the case of implementation in a dry environment (10% RH [Relative Humidity]) and a high humidity environment (80% RH) are illustrated. In the example of FIG. 10, a replica is employed as an example of the skin.

In the example of FIG. 10, the comparison of the volumes [mm³] of wrinkles in the arrowed areas in the dry environment (10% RH) and the high humidity environment (80% RH) shows that residual wrinkles increase in the dry environment while there is no substantial difference between fixed wrinkles and residual wrinkles.

In the example of FIG. 11, wrinkle stresses at the outer corner of an eye in a dry (low humidity) environment (10%

RH) implementation and a high humidity environment (80% RH) implementation are visualized and displayed. In the example of FIG. 11, as a non-limiting example, the image generation part 17 generates images in which stresses in the analysis region 52 are color-coded with preset colors according to size (load level) (a.u.). Alternatively, stresses may be displayed with different patterns or be highlighted in other ways.

In the example of FIGS. 12A through 12C, FIG. 12A illustrates the relationships between the standard deviation values of strain and stress at low humidity (dry environment [10% RH]) and high humidity (high humidity environment [80% RH]), where a higher value indicates that more strain or stress is locally applied. Furthermore, in FIG. 12B, the relationships between the maximum strain and the maximum stress at low humidity (dry environment [10% RH]) and high humidity (high humidity environment [80% RH]) are illustrated. Furthermore, in FIG. 12C, the relationships between the maximum strain (the top 10 average) and the maximum stress (the top 10 average) are illustrated. According to the analysis results of FIGS. 12A through 12C, it is found in each case that greater strain and stress values at low humidity than at high humidity are a cause of residual wrinkles.

[Skin Condition Analysis Process: Example 2 (Wrinkle Parameters Calculation)]

Next, a description is given of Example 2 of the above-described skin condition analysis process in the skin condition analysis part 16. In Example 2, a description is given of an example of calculating wrinkle parameters based on expression wrinkles. In the following description as well, like in Example 1, a description is given using laugh lines as a non-limiting example of expression wrinkles. Alternatively, for example, anger lines, cry lines, or the like may be used.

According to Example 2, for example, two preset tracking points (marks) are put at the outer corner of an eye at a vertical interval of approximately 1.5 cm, and the way the outer corner of the eye moves when a subject laughs is imaged with a high speed camera. Furthermore, the video is decomposed into scenes (frames), and wrinkles are extracted with a preset wrinkle extraction program. According to Example 2, an analysis may be performed by classifying wrinkles into types such as inconspicuous laugh lines and conspicuous laugh lines.

Furthermore, according to Example 2, the relationship between wrinkles and age may be analyzed. As a result, it is possible to discover findings such as the finding that the ratio of conspicuous wrinkles increases with age. Like in Example 1, a cosmetic such as mascara or eyeliner may be used for the tracking points as a non-limiting example.

Figure 13:
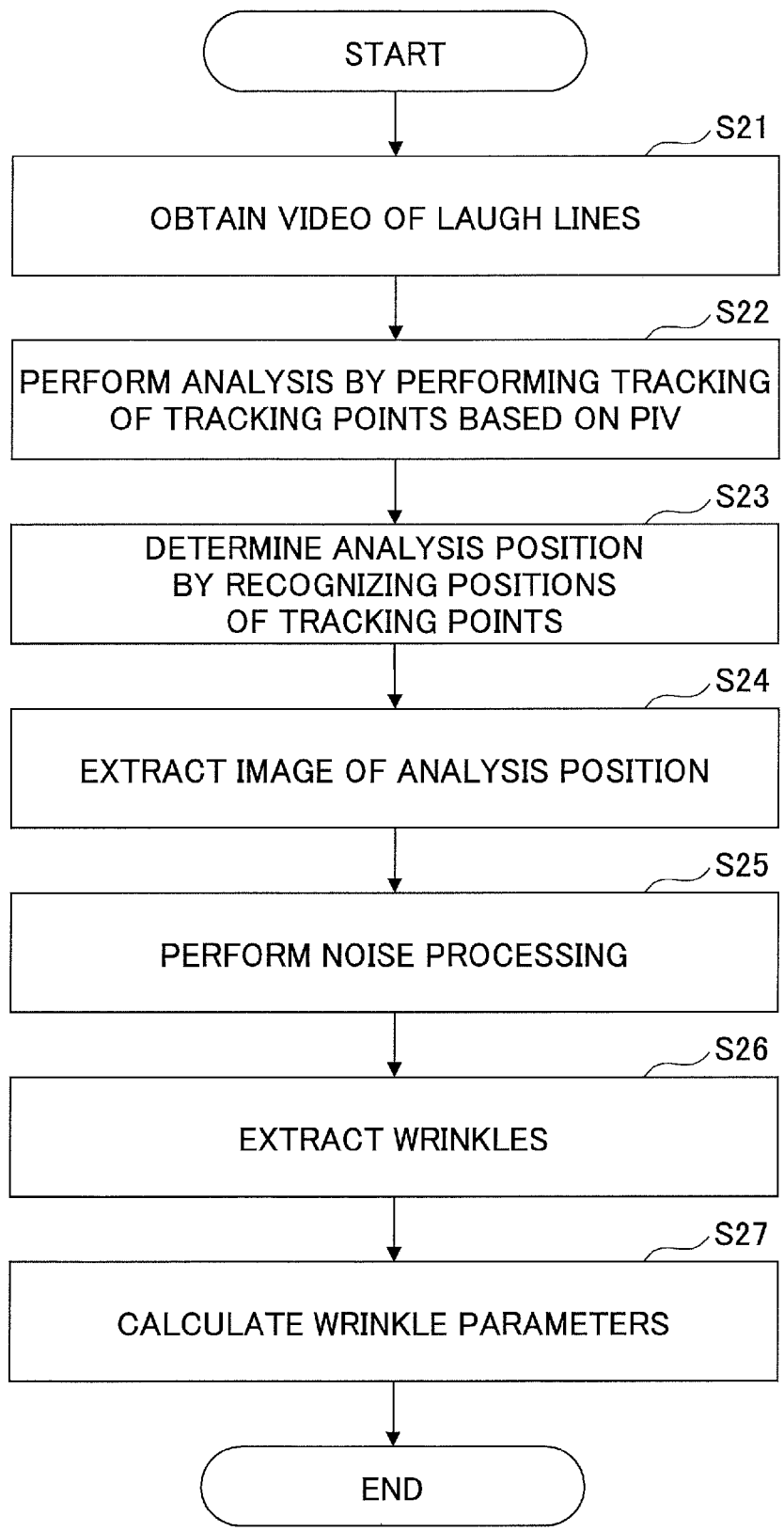
FIG. 13 is a diagram illustrating an example of a skin condition analysis process according to Example 2.

Here, FIG. 13 is a diagram illustrating an example of the skin condition analysis process according to Example 2. Referring to FIG. 13, like in Example 1, the wrinkle parameter calculation part 22 obtains a video at the time when a subject changes her/his expression to have a full smile, using tracking points (marks) provided in the analysis region of the subject as described above (S21).

Next, the wrinkle parameter calculation part 22 performs an analysis by tracking the tracking points based on PIV from the video obtained by the process of S21 (S22). In the process of S22, the positions of the points with respect to each scene of the video may be stored in the storage part 13 in the form of a csv file or a txt file the same as in Example 1. Furthermore, in the process of S22, image processing to decompose the video (for example, in avi file format) into successive still images (for example, a bmp file) may be performed.

Next, the wrinkle parameter calculation part 22 synchronizes the above-described csv file and bmp file images with each other, causes the positions (for example, x and y coordinates) of the tracking points in each bmp file image to be recognized, and determines an analysis position (S23), and extracts a predetermined image (for example, 200 by 200 pixels or for example, approximately 1 cm square) (S24). According to the process of S23, as a non-limiting example, the middle of the two tracking points is recognized as the analysis position. Furthermore, according to Example 2, when the tracking points rotate because of a change in the expression, it is preferable that the position in analysis also be rotated using an inverse affine transformation or the like as a non-limiting example.

Next, the wrinkle parameter calculation part 22 performs preset noise processing (S25), and further extracts wrinkles using a preset wrinkle extraction filter or the like (S26). According to the process of S26, for example, three kinds of wrinkle extraction filters are used to classify wrinkles included in the analysis region into, for example, "fine wrinkles," "large wrinkles," and "conspicuously large wrinkles," but the types are not limited to these. Furthermore, according to the process of S26, noise processing may be performed on the extracted wrinkles. When wrinkles that are not present in the preceding and succeeding frames exist, the wrinkles are highly likely to be noise and may therefore be deleted.

Next, the wrinkle parameter calculation part 22 calculates wrinkle parameters from the wrinkles extracted by the process of S26 (S27). Examples of wrinkle parameters may include, but are not limited to, a wrinkle area, a wrinkle length, a wrinkle ratio, etc.

According to Example 2, a video may be generated by reconstructing successive still images (for example, bmp) into a video (for example, avi or wmv) or the like by the image generation part 17 using the results obtained by the above-described processing, and the generated video may be played. In this case, the image generation part 17 preferably visualizes and highlights the wrinkles extracted by the process of S26 on the original image by color-coding the wrinkles according to the types into which the wrinkles are classified, but the generated image is not limited to this.

Figure 14A:
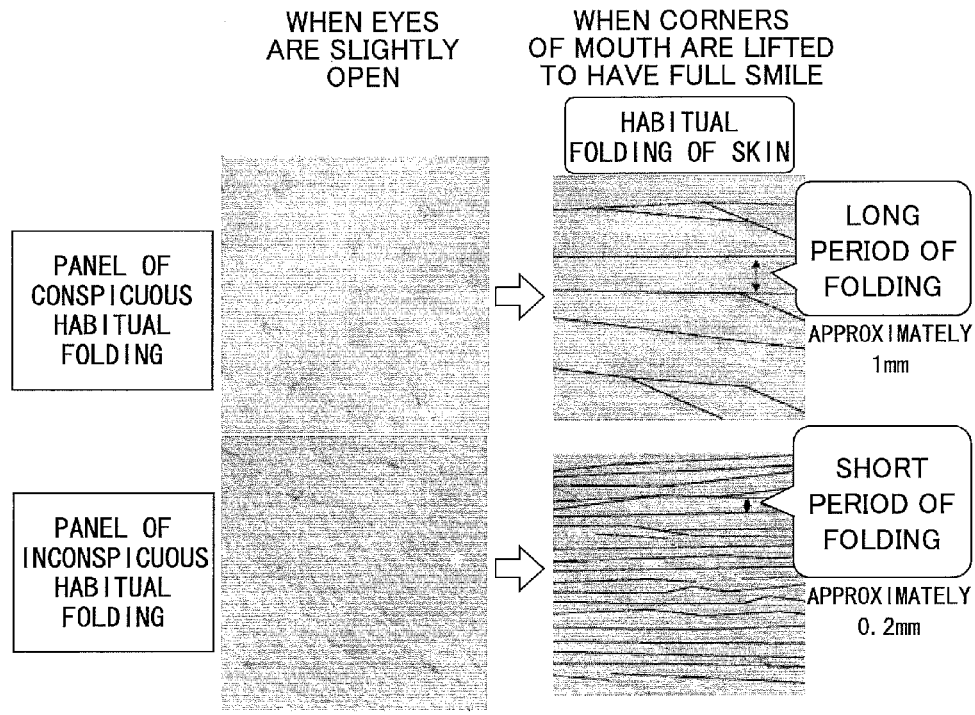
FIGS. 14A and 14B are diagrams for illustrating the habitual folding of expression wrinkles.
Figure 14B:
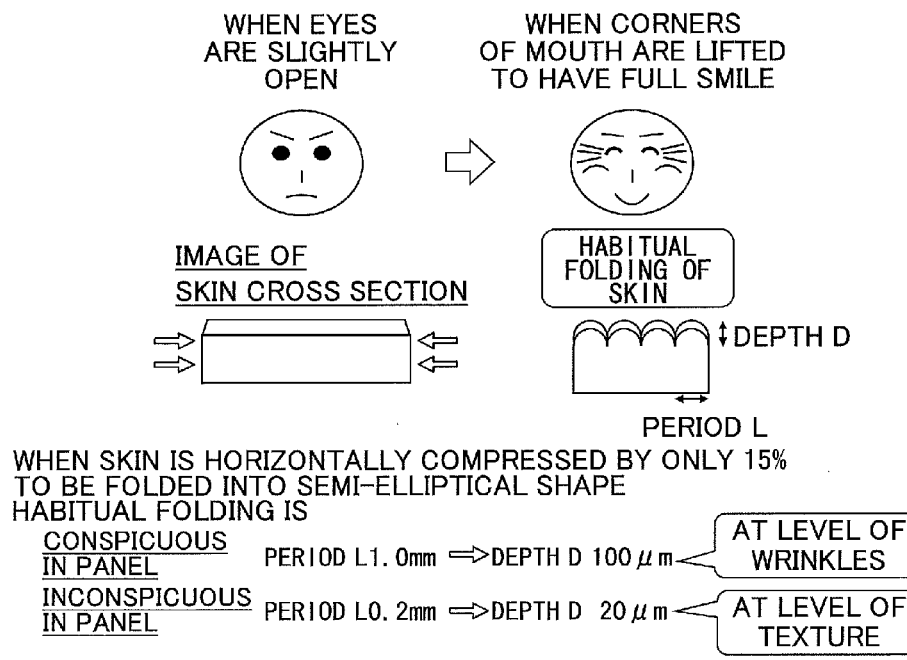

Here, wrinkles depend on the degree of skin's habitual folding. FIGS. 14A and 14B are diagrams for illustrating the habitual folding of expression wrinkles. As illustrated in FIG. 14A, the period of skin's habitual folding differs between the case where the eyes are slightly open and the case where the corners of the mouth are lifted to have a full smile. The period of habitual folding is, but is not limited to, for example, the width of (interval between) two folds as illustrated in FIG. 14A.

As illustrated in FIG. 14A, according to inconspicuous habitual folding, skin is finely folded. Furthermore, letting the depth and the period of the habitual folding be D and L, respectively, in the case where the eyes are slightly open and the case where the corners of the mouth are lifted to have a full smile as illustrated in FIG. 14B, for example, when the skin is horizontally compressed by only 15% to be folded in a semi-elliptical shape, the period L is 1.0 mm and the depth D is 100 μm for the panel (subject) of conspicuous habitual folding as illustrated in FIG. 14A, thus being at the level of "wrinkles." Furthermore, for the inconspicuous panel, the period L is 0.2 mm and the depth D is 20 μm, thus being at the level of "texture." In the above-described examples, the initial state of the skin is determined as being flat, and it is assumed that the individual corneocytes are not deformed by compression. That is, when the skin is finely folded as illustrated in the example of FIGS. 14A and 14B, the habitual folding is shallow and inconspicuous.

Figure 16:
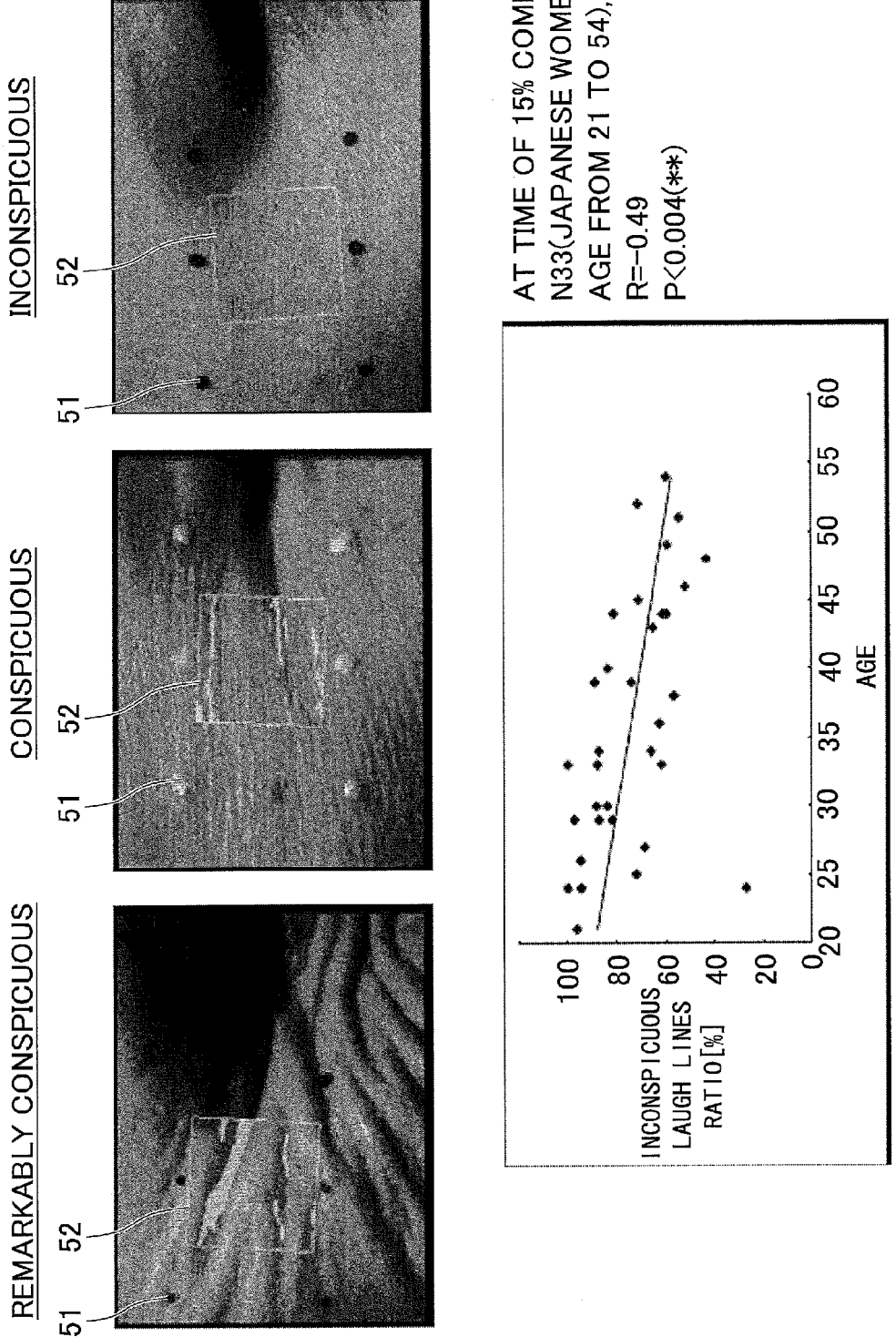
FIG. 16 is a (second) diagram illustrating an analysis result according to Example 2.

Here, FIG. 15 and FIG. 16 are (first and second) diagrams illustrating analysis results according to Example 2. In FIG. 1.5 and FIG. 16, the respective results of three types of wrinkles of "remarkably conspicuous," "conspicuous" and "inconspicuous" are illustrated using preset wrinkle extraction filters. Furthermore, according to the examples of FIG. 15 and FIG. 16, six tracking points 51 are arranged, and wrinkle parameters are calculated with respect to the analysis region 52 of the center quadrangle in the points.

In the example of FIG. 15, the relationship between the compression ratio [%] and "conspicuous laugh lines" that are roughly folded and "inconspicuous laugh lines" that are finely folded is illustrated. It is found from this analysis result that as the skin is more finely folded at the time of laughing, more inconspicuous laugh lines result.

In the example of FIG. 16, the wrinkles classified into "remarkably conspicuous," "conspicuous" and "inconspicuous" are color-coded and displayed. Furthermore, in the case of FIG. 16, the relationship between age and the inconspicuous laugh line ratio [%] is illustrated. It is found from this analysis result that the skin is more finely folded to result in inconspicuous laugh lines at a younger age.

According to the above-described analysis result of Example 2, the images are not limited to the above-described examples, and for example, parameters such as a wrinkle length may be displayed.

The above-described skin condition analysis using expression wrinkles or the like may be applied to, for example, the forehead, the outer corners of the eyes, an area below the outer corners of the eyes, the cheeks, an area around the eyes, an area below the eyes, nasolabial folds, an area between the eyebrows, an area above the nose, etc. FIG. 17 illustrates an analysis result of forehead wrinkles.

In the example of FIG. 17, for example, the analysis results of wrinkles of two subjects (Subject A and Subject B) in the state where the compression ratio of the skin to be analyzed is 0% (a straight face) and where the compression ratio is 20% (such an expression as to lift the forehead) are illustrated.

In the example of FIG. 17, wrinkles that are color-coded according to wrinkle types in the analysis region 52 are illustrated. Furthermore, only images are displayed as a non-limiting example in the example of FIG. 17, while the analysis results of the wrinkles of multiple subjects may be displayed in a time series using video. The above-described images or video is generated by the above-described image generation part 17.

[Skin Condition Analysis Process: Example 3 (Analysis of Skin Twist)]

Application of this embodiment makes it possible to perform not only the above-described stress analysis based on expression wrinkles illustrated in Example 1 but also, for example, a quantitative analysis of the condition of a skin twist generated when the skin is moved with an external force. According to Example 3, it is possible to quantitatively analyze the condition of a twist of the skin of a subject caused at the time of care such as massage or application of an application product (such as foundation), or the like, using the above-described method of calculating wrinkle parameters as illustrated in Example 2, or the like.

Figure 18A:
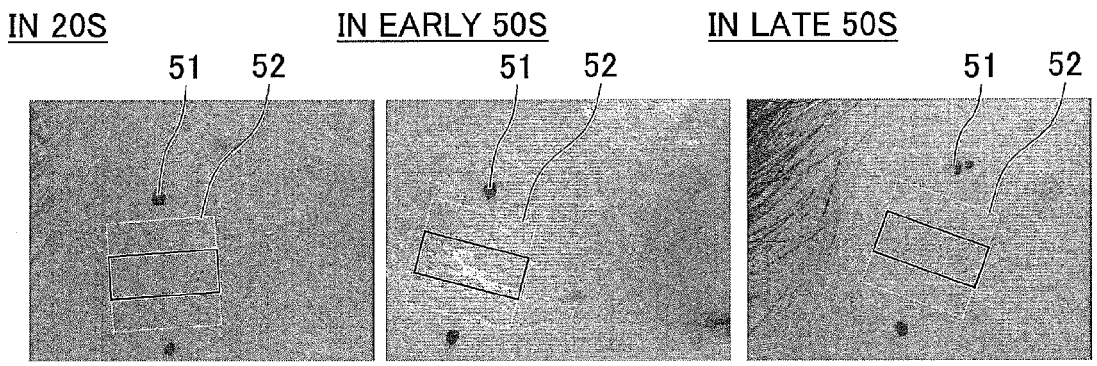
FIGS. 18A through 18C are diagrams illustrating an analysis result according to Example 3.
Figure 18B:
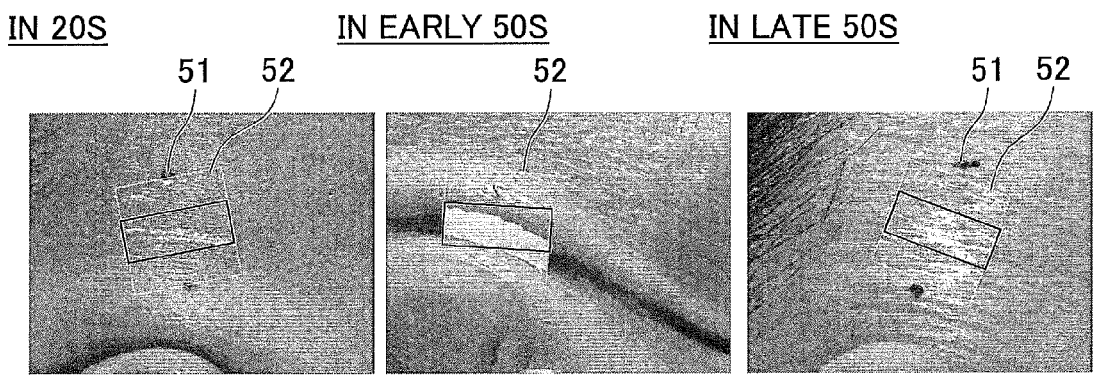
Figure 18C:
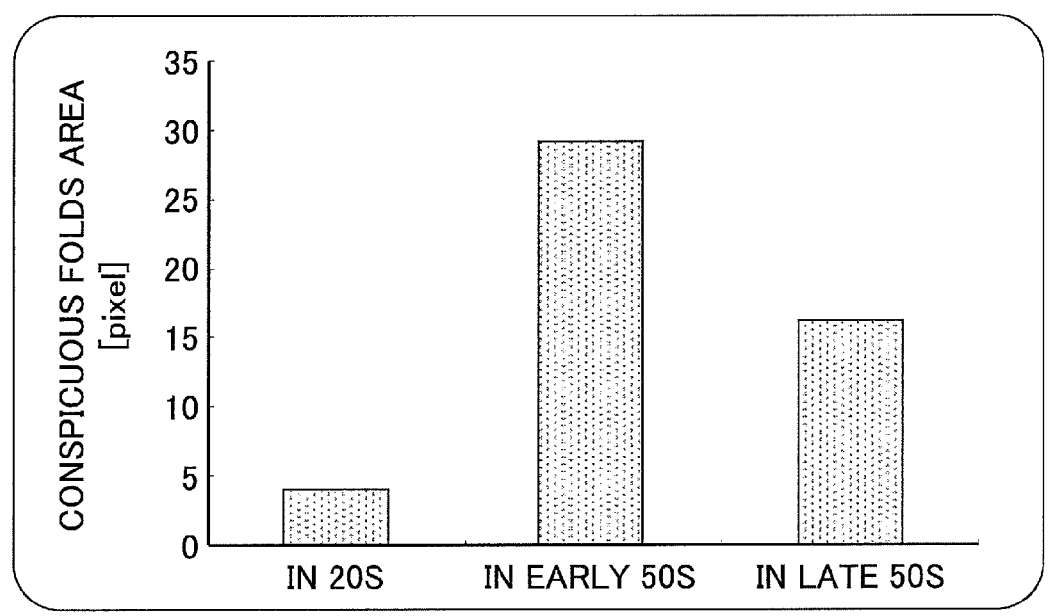

Here, FIGS. 18A through 18C and FIGS. 19A through 19 are (first and second) diagrams illustrating analysis results according to Example 3. FIGS. 18A through 18C illustrate analysis results of a skin twist due to massage based on the ages of subjects. FIGS. 19A through 19C illustrate analysis results of a skin twist with respect to before and after skin care.

FIG. 18A illustrates skin images of subjects of different ages before massage (initial state). FIG. 18B illustrates skin images of the subjects in the state where the skin is massaged with application of a maximum load with a finger or the like (during application of a maximum load). FIG. 18 illustrates the result of adding up areas (pixels) of conspicuous folds in the state of FIG. 18B. In FIGS. 18A through 18C, as examples of the skin images of different ages, those of 20s, early 50s and late 50s are illustrated, while the images are not limited to these kinds.

In the example of FIG. 18A and FIG. 18B, the tracking points 51 are put on the outer corner of an eye and a cheek of a subject with eyeliner or the like, and thereafter, a twist of the skin in the vicinity of the outer corner of the eye (the analysis region 52) at the time of massaging the skin by pressing the predetermined analysis region 52 set in the tracking points 51 in a predetermine direction (for example, in the example of FIGS. 18A through 18C, a bottom (cheek) to top (outer corner of the eye) direction in the images) with a finger or the like is analyzed.

According to Example 3, it is possible for the skin condition analysis part 16 to obtain an analysis result as illustrated in FIG. 18C by, for example, obtaining areas (the number of pixels) analyzed as conspicuous folds based on the skin images illustrated in FIG. 18A and FIG. 18B, the compression ratios obtained by the tracking part 15 or the like, etc. It is possible for the image generation part 17 to, for example, generate an image in which conspicuous folded portions are highlighted using predetermined colors or the like as illustrated in FIG. 18B and generate an image that shows the analysis result illustrated in FIG. 18C and to output the generated images to a screen.

Furthermore, FIG. 19A illustrates the bare skin and the skin condition after skin care (initial state) of the same subject (in late 50s). FIG. 19B illustrates skin images of the bare skin and the skin after skin care in the state where a maximum load is applied with a finger or the like (during application of a maximum load). FIG. 19 illustrates the result of adding up areas (pixels) of conspicuous folds in the state of FIG. 19B. In FIGS. 19A through 19C, the example of the subject in late 50s is illustrated, while the image is not limited to this kind.

In the example of FIG. 19A and FIG. 19B, the tracking points 51 are put at the outer corner of an eye of the subject on the bare skin and the skin after skin care with eyeliner or the like, and thereafter, a twist of the skin in the vicinity of the outer corner of the eye (the analysis region 52) at the time of pressing the predetermined analysis region 52 set in the tracking points 51 in a predetermine direction (for example, in the example of FIGS. 19A through 19C, a bottom (cheek) to top (outer corner of the eye) direction in the images) with a finger or the like is analyzed.

According to Example 3, it is possible for the skin condition analysis part 16 to obtain an analysis result as illustrated in FIG. 19C by, for example, obtaining areas (the number of pixels) analyzed as conspicuous folds based on the skin images illustrated in FIG. 19A and FIG. 19B, the compression ratios obtained by the tracking part 15 or the like, etc. It is possible for the image generation part 17 to, for example, generate an image in which conspicuous folded portions are highlighted using predetermined colors or the like as illustrated in FIG. 19B and generate an image that shows the analysis result illustrated in FIG. 19C and to output the generated images to a screen.

According to Example 3, by using the above-described analysis results, it is possible to, for example, evaluate a better massage method according to age and an application product to be combined with massage.

OTHER EXAMPLES

The images used in the above-described skin condition analysis processes, for which the above-described two-dimensional images captured using a high speed camera or the like are used by way of example, are not limited to these. For example, the above-described analysis and evaluation may be performed using a three-dimensional image into which multiple two-dimensional images obtained from different skin imaging directions are combined, or the like. Some or all of the above-described examples of the skin condition analysis process may be combined.

As described above, according to the present invention, it is possible to properly analyze a skin condition from expression wrinkles of a subject, a twist of the skin at the time of care, or the like. As a result, it is possible to provide services such as providing the subject with new skin care counseling and cosmetic products. In the above-described embodiment, a description is particularly given of an analysis of a facial skin condition as a non-limiting example. Application to an analysis of the skin condition of, for example, other body parts (such as a hand) is also possible.

An expatiation is given above of a preferred embodiment of the present invention. The present invention, however, is not limited to the above-described particular embodiment, and variations and modifications may be made within the scope of the present invention described in the claims.

The present international application is based upon and claims the benefit of priority of Japanese Patent Application No. 2013-070061, filed on Mar. 28, 2013, the entire contents of which are hereby incorporated herein by reference.

DESCRIPTION OF THE REFERENCE NUMERALS 10 image analysis apparatus
11 input part
12 output part
13 storage part
14 image obtaining part
15 tracking part
16 skin condition analysis part
17 image generation part
18 transmission and reception part
19 control part
21 stress analysis part
22 wrinkle parameter calculation part
30 imaging part
41 input device
42 output device
43 drive unit
44 secondary storage device
45 memory
46 CPU
47 network connection device
48 storage part
50 image
51 tracking point (mark)
52 analysis region

The invention claimed is:

1. An image analysis apparatus that analyzes a skin condition from a video of a face of a subject captured with a high speed camera, the image analysis apparatus comprising:
   a processor; and
   a memory storing a program that, when executed by the processor, causes the image analysis apparatus to
   track positions of a plurality of tracking points arranged in advance in an analysis region of the face based on a change in an expression of the face included in the video, and obtain an amount of strain of a skin in the analysis region based on a change in a distance between the plurality of tracking points;
   calculate at least one of an area, a length, and a ratio of a wrinkle with respect to the analysis region based on the tracked positions of the plurality of tracking points; and
   analyze the skin condition of the subject based on the obtained amount of strain and the calculated at least one of the area, the length, and the ratio of the wrinkle.

2. The image analysis apparatus as claimed in claim 1, wherein the program further causes the image analysis apparatus to analyze a stress to the analysis region based on the obtained amount of strain.

3. The image analysis apparatus as claimed in claim 1, wherein the program further causes the image analysis apparatus to analyze a skin twist with respect to the analysis region based on the obtained amount of strain.

4. The image analysis apparatus as claimed in claim 1, wherein the program further causes the image analysis apparatus to generate an image in which a result of analyzing the skin condition of the subject is reflected in an image of the face of the subject captured with the high speed camera.

5. An image analysis method for analyzing a skin condition from a video of a face of a subject captured with a high speed camera, the image analysis method comprising:
   tracking positions of a plurality of tracking points arranged in advance in an analysis region of the face based on a change in an expression of the face included in the video;
   obtaining an amount of strain of a skin in the analysis region based on a change in a distance between the plurality of tracking points;
   calculating at least one of an area, a length, and a ratio of a wrinkle with respect to the analysis region based on the tracked positions of the plurality of tracking points; and
   analyzing the skin condition of the subject based on the obtained amount of strain and the calculated at least one of the area, the length, and the ratio of the wrinkle.

6. The image analysis method as claimed in claim 5, wherein said analyzing analyzes a stress to the analysis region based on the obtained amount of strain.

7. The image analysis method as claimed in claim 5, wherein said analyzing analyzes a skin twist with respect to the analysis region based on the obtained amount of strain.

8. The image analysis method as claimed in claim 5, further comprising:
   generating an image in which an analysis result obtained by said analyzing is reflected in an image of the face of the subject captured with the high speed camera.

9. A non-transitory, computer-readable recording medium storing an image analysis program that, when executed by a processor of a computer, causes the computer to implement the image analysis apparatus as set forth in claim 1.

* * * * *